United States Patent
Zhang et al.

(10) Patent No.: US 9,291,622 B2
(45) Date of Patent: Mar. 22, 2016

(54) COMPLEMENT ASSAYS AND USES THEREOF

(75) Inventors: Zhouning Zhang, Louisville, KY (US); Cedric Francois, Louisville, KY (US); Pascal Deschatelets, Louisville, KY (US); Paul Olson, Louisville, KY (US)

(73) Assignee: Apellis Pharmaceuticals, Inc., Crestwood, KY (US)

( * ) Notice: Subject to any disclaimer, the term of this patent is extended or adjusted under 35 U.S.C. 154(b) by 652 days.

(21) Appl. No.: 13/321,522

(22) PCT Filed: May 21, 2010

(86) PCT No.: PCT/US2010/035871
§ 371 (c)(1),
(2), (4) Date: Feb. 9, 2012

(87) PCT Pub. No.: WO2010/135717
PCT Pub. Date: Nov. 25, 2010

(65) Prior Publication Data
US 2012/0135430 A1   May 31, 2012

Related U.S. Application Data

(60) Provisional application No. 61/230,645, filed on Jul. 31, 2009, provisional application No. 61/180,273, filed on May 21, 2009.

(51) Int. Cl.
*G01N 33/564* (2006.01)
*C07K 16/18* (2006.01)
*G01N 33/68* (2006.01)

(52) U.S. Cl.
CPC .............. *G01N 33/564* (2013.01); *C07K 16/18* (2013.01); *G01N 33/6893* (2013.01); *G01N 2333/4716* (2013.01); *G01N 2800/164* (2013.01); *G01N 2800/52* (2013.01)

(58) Field of Classification Search
CPC ... G01N 33/564; G01N 33/6893; C07K 16/18
See application file for complete search history.

(56) References Cited

U.S. PATENT DOCUMENTS 5,221,616 A * 6/1993 Kolb et al. .................. 435/18
5,981,481 A   11/1999 Fearon et al.
2002/0058614 A1   5/2002 Filvaroff et al.
2005/0281861 A1   12/2005 Hughes et al.
2007/0141573 A1   6/2007 Nunn
2007/0172483 A1   7/2007 Schwaeble et al.
2007/0254322 A1   11/2007 Romaschin et al.
2007/0274989 A1   11/2007 Fung et al.
2009/0111708 A1   4/2009 Seddon et al.
2011/0177957 A1 *  7/2011 Seddon et al. ................. 506/7

FOREIGN PATENT DOCUMENTS

WO   97/33603   9/1997
WO   01/84149 A2   11/2001
WO   2004/026328 A1   4/2004
WO   2007/084765 A2   7/2007

OTHER PUBLICATIONS

Scholl et al. Systemic Complement Activation in Age-Related Macular Degeneration (PLoS ONE 8 (7): 1-7 (Jul. 2008).*
Laursen et al. Bovine Conglutinin binds to an oligosaccharide determinant present by iC3b, but not by C3 or C3b or C3c, Immunology 81: 648-654 (1994).*
Johnson et al., "Complement activation and inflammatory processes in Drusen formation and age related macular degeneration", Exp. Eye Res., 73(6):887-896 (2001).
Mallik et al., "Design and NMR characterization of active analogues of compstatin containing non-natural amino acids", J. Med. Chem., 48(1):274-286 (2005).
Morikis et al., "Solution structure of Compstatin, a potent complement inhibitor", Protein Sci., 7(3):619-627 (1998).
Scholl et al., "Systemic Complement Activation in Age-Related Macular Degeneration", PloS ONE, 3(7):e2593 (2008).
International Search Report for PCT/US2009/038807, mailed Jan. 25, 2010.
Inernational Search Report for PCT/US2010/035871, mailed Feb. 24, 2011.
International Search Report for PCT/US2008/001483, mailed May 23, 2011.
International Preliminary Report on Patentability for PCT/US2010/035871, mailed Dec. 1, 2011.

* cited by examiner

*Primary Examiner* — Gail R Gabel
(74) *Attorney, Agent, or Firm* — Brenda H. Jarrell; Nishat A. Shaikh; Suzanne P. Nguyen

(57) ABSTRACT

The present invention provides methods for assessing complement activation and methods for assessing the ability of an agent or condition of interest to modulate complement activation. The present invention provides methods for assessing whether a subject has or is at increased risk of developing a complement-mediated disorder, e.g., age-related macular degeneration (AMD). Also provided are kits containing materials useful for performing the methods.

20 Claims, 11 Drawing Sheets

User: USER   Path: C:\Program Files\BMG\Omega\User\Data\   File Name: 774.dbf
Test Name: ZZN 450 NM
ID1: HM2073 anti-C3a 100 ng coat UH spiked serum
Absorbance   Absorbance values are displayed as OD

TABLE 2

Raw Data (450)

|   | 1 | 2 | 3 | 4 | 5 | 6 | 7 | 8 | 9 | 10 | 11 | 12 |
|---|---|---|---|---|---|---|---|---|---|---|---|---|
| A | 0.59 | 0.531 | 0.412 | 0.426 | 0.435 | 0.397 | 0.446 | 0.44 | 0.451 | 0.62 | 0.308 | 0.34 |
| B | 0.51 | 0.494 | 0.379 | 0.374 | 0.358 | 0.383 | 0.423 | 0.42 | 0.4 | 0.42 | 0.373 | 0.32 |
| C | 0.4 | 0.366 | 0.376 | 0.405 | 0.33 | 0.301 | 0.29 | 0.31 | 0.296 | 0.31 | 0.24 | 0.23 |
| D | 0.23 | 0.213 | 0.377 | 0.361 | 0.285 | 0.267 | 0.216 | 0.22 | 0.157 | 0.19 | 0.149 | 0.18 |
| E | 0.11 | 0.111 | 0.449 | 0.354 | 0.359 | 0.28 | 0.161 | 0.16 | 0.152 | 0.1 | 0.1 | 0.1 |
| F | 0.08 | 0.066 | 0.377 | 0.358 | 0.281 | 0.276 | 0.127 | 0.15 | 0.08 | 0.08 | 0.062 | 0.06 |
| G | 0.03 | 0.037 |   |   | 0.271 | 0.246 | 0.107 | 0.13 | 0.054 | 0.06 | 0.033 | 0.04 |
| H | 0.041 |   | 0.337 | 0.332 | 0.31 | 0.26 | 0.108 | 0.12 | 0.063 | 0.05 | 0.036 | 0.03 |
| I | 0.04 |   | 0.345 |   | 0.2718 | 0.116 |   | 0.0558 |   |   |   |   |
|   | BB |   | 0.50% |   | 0.10% | 0.05% |   | 0.01% |   | BB |   |   | matrix only
averages for matrix
matrix

TABLE 3

| C3 conc. | C3 in 0.5% serum | C3 in 0.5% serum only | C3 in 0.1% serum | C3 in 0.05% serum | C3 in 0.01% serum | 0.5% serum only |
|---|---|---|---|---|---|---|
| 1 | 0.52 | 0.46 | 0.074 | 0.144 | 0.328 | 0.477 | 0.29 |
| 0.333 | 0.46 | 0.34 | 0.0315 | 0.099 | 0.308 | 0.3515 | 0.309 |
| 0.111 | 0.34 | 0.19 | 0.0455 | 0.044 | 0.186 | 0.2445 | 0.2 |
| 0.037 | 0.19 | 0.07 | 0.024 | 0.004 | 0.101 | 0.118 | 0.129 |
| 0.012 | 0.07 | 0.04 | 0.0565 | 0.048 | 0.046 | 0.071 | 0.063 |
| 0.004 | 0.04 | -0 | 0.0225 | 0.007 | 0.02 | 0.022 | 0.023 |
| 0.0014 | -0 |   | 0.02 | -0.014 | 1E-03 | -0.002 | -1E-03 |

FIG. 3b

User: USER    Path: C:\Program Files\BMG\Omega\User\Data\    File Name: 773.dbf
Test Name: ZZN 450 NM    Time: 4:42:15 PM
ID1:HM2073 anti-C3a 100 ng coat UH spiked serum
Absorbance    Absorbance values are displayed as OD

TABLE 4

Raw Data (450)

|   | 1 | 2 | 3 | 4 | 5 | 6 | 7 | 8 | 9 | 10 | 11 | 12 |
|---|---|---|---|---|---|---|---|---|---|---|---|---|
| A | 0.477 | 0.471 | 0.481 | 0.46 | 0.475 | 0.491 | 0.443 | 0.472 | 0.425 | 0.455 | 0.392 | 0.379 |
| B | 0.301 | 0.302 | 0.446 | 0.451 | 0.379 | 0.376 | 0.275 | 0.313 | 0.288 | 0.281 | 0.312 | 0.316 |
| C | 0.17 | 0.148 | 0.448 | 0.419 | 0.32 | 0.314 | 0.161 | 0.173 | 0.158 | 0.156 | 0.172 | 0.18 |
| D | 0.084 | 0.089 | 0.448 | 0.444 | 0.279 | 0.293 | 0.099 | 0.109 | 0.088 | 0.086 | 0.089 | 0.086 |
| E | 0.05 | 0.05 | 0.41 | 0.414 | 0.254 | 0.25 | 0.078 | 0.08 | 0.096 | 0.056 | 0.054 | 0.052 |
| F | 0.048 | 0.044 | 0.413 | 0.295 | 0.257 | 0.257 | 0.07 | 0.073 | 0.048 | 0.047 | 0.041 | 0.04 |
| G | 0.031 | 0.033 | 0.412 | 0.41 | 0.264 | 0.259 | 0.065 | 0.068 | 0.042 | 0.038 | 0.029 | 0.032 | matrix only
| H | 0.033 | 0.03 | 0.404 | 0.418 | 0.253 | 0.267 | 0.068 | 0.069 | 0.045 | 0.038 | 0.03 | 0.03 |
| I | 0.031 |   | 0.411 |   | 0.2608 |   | 0.0675 |   | 0.0408 |   | 0.03 |   | averages for matrix
|   | BB |   | 0.50% | 0.10% | 0.01% | 0.05% |   |   |   |   | BB |   |

TABLE 5

| C3 conc. | C3 | C3 in 0.5% serum | C3 in 0.1% serum | C3 in 0.05% serum | C3 in 0.01% serum | C3 in 0.5% serum only |
|---|---|---|---|---|---|---|
| 1 | 0.443 | 0.0595 | 0.222 | 0.39 | 0.399 | 0.355 |
| 0.333 | 0.271 | 0.0375 | 0.117 | 0.226 | 0.2435 | 0.283 |
| 0.111 | 0.128 | 0.0226 | 0.056 | 0.099 | 0.116 | 0.145 |
| 0.037 | 0.056 | 0.035 | 0.025 | 0.036 | 0.046 | 0.057 |
| 0.012 | 0.019 | 0.001 | -0.009 | 0.011 | 0.035 | 0.022 |
| 0.004 | 0.015 | -0.057 | -0.004 | 0.004 | 0.0065 | 0.01 |
| 0.0014 | 0.001 | 0 | 5E-04 | -0 | -0.001 | -5E-04 |

*FIG. 3d*

TABLE 6

User: USER  Path: C:\Program Files\BMG\Omega\User\Data\  File Name: 870.dbf
Test Name: ZZN 450 NM  Time: 4:39:38 PM
ID1:iC3b assay human vitreous
Absorbance  Absorbance values are displayed as OD Raw Data (450)

|  | 1 | 2 | 3 | 4 | 5 | 6 | 7 | 8 | 9 | 10 | 11 | 12 | matrix only average |
|---|---|---|---|---|---|---|---|---|---|---|---|---|---|
| iC3b in blocker A | 0.371 | 0.258 | 0.169 | 0.106 | 0.064 | 0.053 | 0.043 | 0.035 | 0.033 | 0.03 | 0.032 | 0.0298 BB |
| iC3b in blocker B | 0.344 | 0.265 | 0.167 | 0.1 | 0.07 | 0.048 | 0.038 | 0.032 | 0.028 | 0.028 | 0.028 | |
| iC3b 30% vitreous C | 0.443 | 0.406 | 0.391 | 0.385 | 0.375 | 0.355 | 0.336 | 0.368 | 0.335 | 0.35 | 0.362 | 0.3608 30% vitreous |
| iC3b 30% vitreous D | 0.453 | 0.406 | 0.433 | 0.391 | 0.362 | 0.356 | 0.355 | 0.362 | 0.375 | 0.377 | 0.366 | |
| iC3b 20% vitreous E | 0.485 | 0.442 | 0.411 | 0.361 | 0.353 | 0.339 | 0.321 | 0.264 | 0.303 | 0.326 | | 0.3238 20% vitreous |
| iC3b 20% vitreous F | 0.527 | 0.45 | 0.435 | 0.384 | 0.355 | 0.333 | 0.318 | 0.38 | 0.332 | 0.334 | | |
| iC3b 10% vitreous G | 0.508 | 0.385 | 0.28 | 0.274 | 0.254 | 0.248 | 0.227 | 0.229 | 0.259 | 0.236 | 0.227 | 0.2255 10% vitreous |
| iC3b 10% vitreous H | 0.42 | 0.316 | 0.283 | 0.3 | 0.23 | 0.231 | 0.237 | 0.207 | 0.201 | 0.225 | 0.205 | |

TABLE 7
iC3b conc.:

|  | 1 | 0.5 | 0.25 | 0.125 | 0.063 | 0.031 | 0.016 | 0.0078 |
|---|---|---|---|---|---|---|---|---|
| iC3b in blocker | 0.328 | 0.232 | 0.138 | 0.073 | 0.037 | 0.021 | 0.011 | #REF! |
| iC3b in 30% vitreous | 0.087 | 0.045 | 0.051 | 0.027 | 0.008 | -0.005 | -0.02 | 0.0042 |
| iC3b in 20% vitreous | 0.182 | 0.122 | 0.099 | 0.049 | 0.03 | 0.012 | -0 | -0.002 |
| iC3b in 10% vitreous | 0.239 | 0.125 | 0.056 | 0.062 | 0.017 | 0.014 | 0.006 | -0.008 |

*FIG. 8b*

COMPLEMENT ASSAYS AND USES THEREOF

RELATED APPLICATIONS

The present application is the National Stage application under 35 U.S.C. §371 of International Application No. PCT/US2010/035871, filed May 21, 2010, which claims priority to, and benefit of, U.S. provisional patent application Nos. U.S. Ser. No. 61/180,273 (filed May 21, 2009) and U.S. Ser. No. 61/230,645 (filed Jul. 31, 2009), the entire contents of each of which are herein incorporated by reference.

SEQUENCE LISTING

The present specification makes reference to a Sequence Listing (submitted electronically as a .txt file named "2008575-0032_Sequence_Listing" on Jan. 25, 2016. The .txt file was generated on Jan. 24, 2016 and is 14 kilobytes in size. The entire contents of the Sequence Listing are herein incorporated by reference.

BACKGROUND OF THE INVENTION

The complement system comprises more than 30 serum and cellular proteins and has important roles in innate and adaptive immunity (Walport, M., N Engl J Med.; 344(14): 1058-66, 2001). Complement activation can occur via three major pathways: the classical, alternative, and lectin pathways. The classical pathway is typically triggered by binding of a complex of antigen and IgM or IgG antibody to complement component C1. Activated C1 cleaves components C4 and C2 to produce C4a and C4b, in addition to C2a and C2b. C4b and C2a combine to form the classical pathway (CP)C3 convertase, which cleaves C3 to form C3a and C3b. Binding of C3b to C3 convertase produces a C5 convertase. The alternative pathway (AP) is typically activated by targets such as microbial surfaces and various complex polysaccharides and other materials. This pathway can be initiated by spontaneous cleavage of the thioester bond in C3 to form $C3(H_2O)$. $C3(H_2O)$ binds factor B, which allows factor D to cleave factor B to Ba and Bb. Bb remains associated with $C3(H_2O)$ to form the $C3(H_2O)Bb$ complex, which acts as a C3 convertase and cleaves C3, resulting in C3a and C3b. C3b formed either via this process or via the classical or lectin pathways binds to targets, e.g., on cell surfaces, and forms a complex with factor B, which is later cleaved by factor D to form Bb, resulting in a C3 convertase. This alternative pathway convertase is also termed C3bBb. Binding of another molecule of C3b to the C3 convertase produces a C5 convertase. The lectin complement pathway is initiated by binding of mannose-binding lectin (MBL) and MBL-associated serine protease (MASP) to carbohydrates. The MB1-1 gene (known as LMAN-1 in humans) encodes a type I integral membrane protein localized in the intermediate region between the endoplasmic reticulum and the Golgi. The MBL-2 gene encodes the soluble mannose-binding protein found in serum. In the human lectin pathway, MASP-1 and MASP-2 are involved in proteolysis of C4 and C2, leading to a C3 convertase, which leads to production of a C5 convertase as described above for the classical pathway.

C5 convertases generated via any of the pathways cleave C5 to produce C5a and C5b. C5b then binds to C6, C7, and C8 to form C5b-8, which catalyzes polymerization of C9 to form the C5b-9 membrane attack complex (MAC). The MAC inserts itself into target cell membranes and causes cell lysis. Sub-lytic amounts of MAC on the membrane of cells may affect cell function in a variety of ways. The small cleavage products C3a, C4a, and C5a are anaphylotoxins and mediate multiple reactions in the acute inflammatory response. C3a and C5a are also chemotactic factors that attract immune system cells such as neutrophils. All three anaphylatoxins contain carboxyl-terminal arginine residues that are rapidly removed by carboxypeptidases in whole blood or serum. The desarginine derivatives of C3a and C4a exhibit minimal binding to the C3a receptor. In the case of C5a, the biologic activity and decreases by more than an order of magnitude.

Deficiencies and functional disorders in complement components or regulatory proteins are responsible for a number of disorders. It is also increasingly recognized that excessive or inappropriate complement activation plays an important pathogenic role in a wide variety of diseases and clinical conditions. A variety of assays have been developed for studying the complement system, diagnosing complement deficiencies and complement-mediated disease, and developing agents to modulate the complement system. Hemolysis-based techniques may be used to measure the functional activity of the entire complement cascade. Classical or alternative complement pathway activation may be assessed by measuring complement-mediated hemolysis of erythrocytes (e.g., antibody-sensitized or unsensitized sheep or rabbit erythrocytes) by human serum or by a set of complement components. For example, to measure the functional capacity of the classical pathway, sheep red blood cells coated with hemolysin (rabbit IgG to sheep red blood cells) are typically used as target cells (sensitized cells). These Ag-Ab complexes activate the classical pathway and result in lysis of target cells when the complement components are functional and present in sufficient concentration. To determine the functional capacity of the alternative pathway, rabbit red blood cells are typically used as the target cell.

A variety of immunological techniques have been developed to measure the concentration of a particular complement component or cleavage product. Antibodies have been raised against different epitopes of various (human) complement components and their major cleavage products. Radioimmunoassays, radial diffusion assays, and enzyme-linked immunosorbent assays (ELISAs) have been developed to detect these molecules. Descriptions of various methods that have been employed in efforts to measure complement activation are found in Wurzer, R., "Immunochemical Measurement of Complement Components and Activation Products", pp. 103-112, in Complement Methods and Protocols (Methods in Molecular Biology) Humana Press; 1 edition, 2000, in the review article by Mollnes, T., et al., "Complement analysis in the $21^{st}$ century", Mol. Immunol., 44: 3838-3849, 2007, and references therein, all of which are incorporated herein by reference.

SUMMARY OF THE INVENTION

The present invention provides methods for assessing the level of intact complement component C3 in a sample. The invention also provides methods for assessing the level of iC3b in a sample and methods for assessing the amount of total C3 in a sample. The methods may be used individually, or two or more methods may be used together, as described further below. In some embodiments the sample comprises blood, plasma, or serum. In some embodiments the sample comprises aqueous humor or vitreous humor. In some embodiments the sample was obtained from a human subject. In some embodiments the sample was obtained from a subject suffering from AMD. In some embodiments the subject has not been previously diagnosed as having AMD. In some embodiments the subject has been previously diagnosed as having dry AMD and not wet AMD. In some embodiments the subject has been previously diagnosed as having early AMD and not geographic atrophy (GA). In some embodiments the subject has been previously diagnosed as having GA in one eye and not the other eye. In some embodiments the subject has been previously diagnosed as having GA not involving the fovea.

The invention further provides a method for assessing whether a subject has, or is at increased risk of developing, age-related macular degeneration (AMD), or is at increased risk of progressing from early AMD to more advanced AMD, comprising detecting intact C3 in a sample comprising serum, plasma, or blood from the subject, wherein a level of intact C3 that is greater than a control level indicates that the individual has or is at increased risk of developing AMD, or is at increased risk of progressing from early AMD to more advanced AMD.

The invention further provides a method for assessing whether a subject has or is at increased risk of developing age-related macular degeneration (AMD) comprising determining the level of one or more proteins in a sample comprising serum, plasma, or blood from the subject using a monoclonal antibody that binds to C3a, wherein a level of said one or more proteins that is greater than a control level indicates that the individual has or is at increased risk of developing AMD.

In some aspects, the invention provides methods of assessing complement activation. In some aspects, the invention provides a method of assessing complement activation in a sample comprising determining the amount of iC3b, the ratio of iC3b to intact C3, or the fraction of C3 that is intact in the sample. In some embodiments the method comprises determining the ratio of iC3b to intact C3 in the sample. In some embodiments the sample comprises whole blood, plasma, or serum. In some embodiments the sample comprises aqueous humor or vitreous humor. In some embodiments the sample was obtained from a human subject. In some embodiments the sample was obtained from a subject having or suspected of having a complement deficiency or complement-mediated disease or condition. In some embodiments the sample was obtained from a subject suffering from AMD. In some embodiments the subject suffers from early AMD. In some embodiments the subject has a genotype associated with increased risk of developing AMD. In some embodiments the sample was obtained from a subject who has recently suffered severe injury, stroke, asthma exacerbation, cardiac arrest, or heart attack. In some embodiments the sample was obtained from a subject who has been treated with a complement inhibitor. In some embodiments the sample comprises an agent being assessed for its ability to modulate complement activation. In some embodiments the method comprises steps of: (a) determining the concentration of intact C3 present in the sample; (b) determining the concentration of iC3b present in the sample; and (c) calculating the ratio of iC3b to intact C3 in the sample using the results of steps (a) and (b). In some embodiments the method comprises steps of: (a) determining the concentration of intact C3 present in the sample; (b) determining the concentration of total C3 present in the sample; and (c) calculating the fraction of C3 that is intact in the sample using the results of steps (a) and (b). In some embodiments the method comprises steps of: (a) capturing intact C3 present in one or more sub-samples of the sample using a first capture agent that binds to intact C3; (b) quantifying intact C3 captured in step (a); (c) capturing iC3b present in one or more sub-samples of the sample using a second capture agent that binds to a neoepitope of iC3b; (d) quantifying iC3b captured in step (c); and (e) calculating the ratio of iC3b to intact C3 in the sample using the results of steps (b) and (d). In some embodiments the method comprises steps of: (a) capturing intact C3 present in one or more sub-samples of the sample using a first capture agent that binds to intact C3; (b) quantifying intact C3 captured in step (a); (c) capturing total C3 present in one or more sub-samples of the sample using a second capture agent that binds to total C3; (d) quantifying total C3 captured in step (c); and (e) calculating the fraction of C3 that is intact in the sample using the results of steps (b) and (d). In some embodiments of a method that employs a capture agent, the first capture agent, the second capture agent, or both, are each immobilized on a support. In some embodiments the support comprises a microwell plate. In some embodiments the support comprises a plurality of particles. In some embodiments of a method that employs a capture agent, e.g., the capture agent of step (a), step (c), or both comprises an antibody. In some embodiments a capture agent that binds to intact C3 comprises an antibody that binds to C3a. Such an antibody is sometimes referred to herein as binding to C3a/C3, indicating that the antibody binds to the C3a portion of C3 and recognizes its epitope when present in intact C3. In some embodiments the antibody is monoclonal. In some embodiments a capture agent that binds to a neoepitope of iC3b comprises an antibody that binds to a neoepitope of iC3b. In some embodiments the antibody is monoclonal. In some embodiments a capture agent that binds to total C3 comprises an antibody that binds to C3d. In some embodiments intact C3 is detected and optionally quantified using a detection agent that specifically binds to C3a. In some embodiments an inventive method comprises comprises capturing intact C3 using a monoclonal antibody that binds to C3a, and detecting intact C3 using a polyclonal antibody that binds to C3. In some embodiments an inventive method comprises capturing iC3b using a monoclonal antibody that binds to a neoepitope of iC3b and detecting iC3b using a polyclonal antibody that binds to C3. In some embodiments a capture agent that binds to total C3 is a polyclonal antibody that binds to C3d and a specific binding agent for detecting intact C3 is a monoclonal antibody that binds to C3a. In some embodiments the method comprises detecting total C3 using a detection agent that binds to total C3. In some embodiments the detection agent for detecting total C3 comprises a monoclonal antibody that binds to C3d. In some embodiments the method the detection agent for detecting total C3 comprises a polyclonal antibody that binds to C3. In some embodiments the method comprises determining the ratio of iC3b to intact C3, further comprising determining the concentration of total C3 in the sample.

In another aspect, the invention provides a method of assessing complement activation in a sample comprising: (a) capturing and detecting intact C3, wherein intact C3 is captured using an antibody that binds to C3a but does not bind to other C3 fragments; and (b) capturing and detecting iC3b, wherein iC3b is captured using an antibody that binds to a neoepitope of iC3b, and wherein the ratio of iC3b to intact C3 serves as an indicator of the extent of complement activation, with a higher ratio indicating a greater extent of complement activation. In some embodiments the antibody that binds to C3a is a monoclonal antibody. In some embodiments the antibody that binds to iC3b is a monoclonal antibody. In some embodiments the detection agent used to detect intact C3 is the same as the detection agent used to detect iC3b, e.g., in different wells. In some embodiments intact C3 and iC3b are each detected using a polyclonal antibody. In some embodiments the polyclonal antibody binds to C3. In some embodiments intact C3 is captured using an antibody that binds to C3a and is detected using an antibody that binds to C3. In some embodiments intact C3 is captured using a monoclonal antibody that binds to C3a and is detected using a polyclonal antibody that binds to C3. In some embodiments intact C3 is captured using a monoclonal antibody that binds to C3a and is detected using a polyclonal antibody that binds to C3d. In some embodiments iC3b is captured using a monoclonal antibody that binds to a neoepitope of iC3b and is detected using a polyclonal antibody that binds to C3. In some embodiments total C3 is captured using a polyclonal antibody that binds to C3d and is detected using a monoclonal antibody that binds to C3d. In some embodiments intact C3 is captured using a monoclonal antibody that binds to C3a and is detected using a polyclonal antibody that binds to C3, and iC3b is captured using a monoclonal antibody that binds to a neoepitope of iC3b and is detected using a polyclonal antibody that binds to C3. In some embodiments the same polyclonal antibody is used to detect intact C3 and to detect iC3b. In some embodiments one or more capture antibody(ies) is/are attached to supports. In some embodiments the sample comprises serum or plasma. In some embodiments the sample comprises aqueous or vitreous humor. In some embodiments the sample was obtained from a human subject. In some embodiments the sample was obtained from a subject having or suspected of having a complement deficiency or complement-mediated disease or condition. In some embodiments the sample was obtained from a subject suffering from AMD. In some embodiments the sample was obtained from a subject who has recently suffered severe injury. In some embodiments the sample was obtained from a subject being treated with a complement inhibitor. In some embodiments the sample comprises an agent being assessed for its ability to modulate complement activation.

In another aspect the invention provides methods of assessing complement activation in a subject comprising steps of: (a) providing a biological sample obtained from the subject; and (b) assessing complement activation in the sample according to an inventive method described above or described elsewhere herein. In some embodiments the method further comprises (c) using the result of step (b) to provide diagnostic, prognostic, or treatment-related information regarding the subject.

In another aspect, the invention provides a kit comprising: (a) a capture agent that binds to intact C3 and does not bind to C3b or iC3b; (b) a capture agent that binds to a neoepitope of iC3b; and (c) a detection agent that binds to intact C3 and (d) a detection agent that binds to iC3b. In some embodiments the capture agent of (a) comprises a monoclonal antibody that binds to C3a. In some embodiments the capture agent of (b) comprises a monoclonal antibody that binds to a neoepitope of iC3b. In some embodiments the detection agent of (c) and the detection agent of (d) are the same. In some embodiments the detection agent that binds to intact C3 comprises an antibody that binds to C3. In some embodiments the antibody that binds to C3 is a polyclonal antibody. In some embodiments the kit comprises (i) a polyclonal antibody that binds to C3; and (ii) a monoclonal antibody that binds to C3a. In some embodiments the kit comprises (i) a monoclonal antibody that binds to a neoepitope of iC3b; and (ii) a monoclonal antibody that binds to C3a. In some embodiments the kit comprises (i) a polyclonal antibody that binds to C3; (ii) a monoclonal antibody that binds to a neoepitope of iC3b; (iii) and a monoclonal antibody that binds to C3a. The invention provides a kit comprising: (a) a capture agent that binds to intact C3 and does not bind to C3b or iC3b; and (b) a detection agent that binds to intact C3. In some embodiments the capture agent of (a) comprises a monoclonal antibody that binds to C3a. In some embodiments the monoclonal antibody is HM2075 or a monoclonal antibody that binds to the same epitope as HM2075. In some embodiments the monoclonal antibody is HM2073 or a monoclonal antibody that binds to the same epitope as HM2073. In some embodiments the detection agent of (b) comprises a polyclonal antibody that binds to C3. In some embodiments the polyclonal antibody does not bind to C3a. In some embodiments the polyclonal antibody was raised against C3d. In some embodiments a kit of the invention further comprises at least one item selected from the group consisting of: instructions for use of the kit; one or more native complement components or cleavage products; human serum complement, optionally characterized for levels of one or more complement components or cleavage products; serum depleted of one or more complement components; a detectably labeled secondary antibody; an enzyme substrate; a buffer; and a support. In some embodiments the detectably labeled secondary antibody is labeled with an enzyme. In some embodiments the kit comprises one or more proteins selected from the group consisting of: C3 protein; C3d polypeptide; C3b polypeptide; and iC3b polypeptide. Instructions for use of the kit can comprise, e.g., instructions for assessing the level of intact C3, instructions for assessing the level of iC3b, instructions for assessing the level of total C3, instructions for assessing complement activation. Instructions can also or alternately comprise information regarding interpretation of the results of performing an assay using the kit. For example, such instructions may indicate that an increased level of intact C3 in a serum, plasma, or blood sample obtained from a subject is indicative that the subject has or is likely to develop clinically evident AMD.

Unless otherwise stated, the invention makes use of standard methods of molecular biology, immunology, antibody production, etc., and uses art-accepted abbreviations and meanings of terms. This application refers to various patents and publications. The contents of all scientific articles, books, patents, patent applications, and other publications, mentioned in this application are incorporated herein by reference. In addition, the following publications are incorporated herein by reference: *Current Protocols in Molecular Biology, Current Protocols in Immunology, Current Protocols in Protein Science*, and *Current Protocols in Cell Biology*, all John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001; Kuby Immunology, 6th ed., Kindt, T. J., et al (eds.), W.H. Freeman, 2006, *Goodman and Gilman's The Pharmacological Basis of Therapeutics*, 11$^{th}$ Ed., McGraw Hill, 2005, Katzung, B. (ed.) *Basic and Clinical Pharmacology*, McGraw-Hill/Appleton & Lange; 10th edition, 2006; Goldman & Ausiello, *Cecil Textbook of Medicine*, 23rd ed., W.B. Saunders, 2007; Paul, W. (ed.) Fundamental Immunology, 6$^{th}$ edition, Lippincott Williams and Wilkins, Philadelphia, Pa. 2008.

BRIEF DESCRIPTION OF THE DRAWING

FIG. 1a shows intact C3, composed of beta and alpha chains linked by a disulfide bond. The alpha chain has an intramolecular disulfide bond. C3 convertases cleave intact C3 to yield C3a and C3b (FIG. 1b). Further cleavage removes C3f, resulting in iC3b, which is inactive (FIG. 1c). Next, C3dg is removed from iC3b, resulting in C3c (FIG. 1d). C3dg is cleaved into C3d and C3g fragments (FIG. 1e).

FIG. 2a shows results of an ELISA assay in which anti-human C3a mAb A203 (Quidel) was used as capture antibody. The ELISA plate was coated with 100 ng/well mouse anti-C3a. FIG. 2b shows results of an ELISA assay in which anti-human C3a mAb HM 2075 (Cell Science) was used as capture antibody. The plate was coated with 50 ng/well mouse anti-C3a.

FIG. 3a shows results of an ELISA assay in which anti-human C3a mAb HM 2075 (Cell Science) was used as capture antibody. The plate was coated with 100 ng/well mouse anti-C3a. FIG. 3b shows the raw and processed data in Tables 2 and 3, respectively. FIG. 3c shows results of an ELISA assay in which anti-human C3a mAb HM 2073 (Cell Science) was used as capture antibody. The plate was coated with 100 ng/well mouse anti-C3a. FIG. 3d shows the raw and processed data shown in Tables 4 and 5, respectively. In each case, goat anti-C3-HRP was used as detection antibody.

FIG. 8b shows the raw and processed data in Tables 6 and 7, respectively.

DETAILED DESCRIPTION OF CERTAIN EMBODIMENTS OF THE INVENTION

Figure 1:
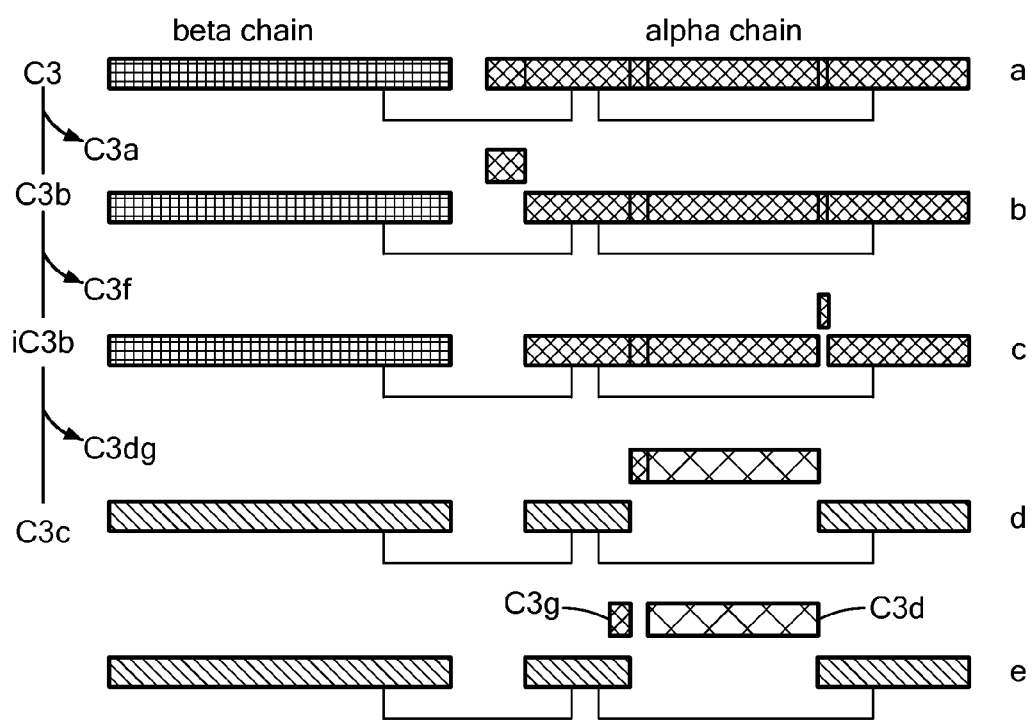
FIG. 1 is a schematic diagram showing steps in the pathway of C3 activation and inactivation.

This invention is not limited to particularly exemplified systems or parameters as such may, of course, vary. The terminology used herein is for the purpose of describing particular embodiments of the invention and is not intended to limit the scope of the invention in any manner. The definitions below are provided for the convenience of the reader and are not intended to conflict with the usage of such terms in the art unless specifically indicated.

I. Definitions

"Analyte" means any entity, particularly a chemical, biochemical or biological entity to be assessed, e.g., whose amount (e.g., concentration or mass), activity, composition, or other property(ies) is/are to be detected, measured, quantified, evaluated, analyzed, etc. An "analyte" can be a single molecular species or can be composed of multiple distinct molecular species.

"Antibody" encompasses intact and/or full length immunoglobulins of types IgA, IgG (e.g., IgG1, IgG2, IgG3, IgG4), IgE, IgD, IgM, IgY, antigen-binding fragments or single chains of complete immunoglobulins (e.g., single chain antibodies, Fab fragments, F(ab')2 fragments, Fd fragments, scFv (single-chain variable), and dAb fragments), and other proteins that include at least one antigen-binding immunoglobulin variable region, e.g., a protein that comprises an immunoglobulin variable region, e.g., a heavy (H) chain variable region (VH) and a light (L) chain variable region (VL). The light chains of an antibody may be of type kappa or lambda. An antibody may be polyclonal or monoclonal. A polyclonal antibody contains immunoglobulin molecules that differ in sequence of their complementarity determining regions (CDRs) and, therefore, typically recognize different epitopes of an antigen. Often a polyclonal antibody is derived from multiple different B cell lines each producing an antibody with a different specificity. A polyclonal antibody may be composed largely of several subpopulations of antibodies, each of which is derived from an individual B cell line. A monoclonal antibody is composed of individual immunoglobulin molecules that comprise CDRs with the same sequence, and, therefore, recognize the same epitope (i.e., the antibody is monospecific). Often a monoclonal antibody is derived from a single B cell line or hybridoma. An antibody may be a "humanized" antibody in which for example, a variable domain of rodent origin is fused to a constant domain of human origin or in which some or all of the complementarity-determining region amino acids often along with one or more framework amino acids are "grafted" from a rodent, e.g., murine, antibody to a human antibody, thus retaining the specificity of the rodent antibody.

"Approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value).

"Assay composition" refers to a composition on which an inventive method for assessing complement activation is performed, i.e., a composition whose concentration of intact C3 and total C3 is measured. An assay composition often comprises a biological sample and one or more fluid diluents, such as water. A variety of other substances may be included in an assay composition such as salts, solvents, buffers, detergents, neutral proteins, e.g. albumin, etc., which may be used to facilitate specific binding interactions, maintain protein stability, reduce non-specific or background interactions, etc. An assay composition may also comprise one or more specific binding agents for use in carrying out detection and/or one or more substances that modulate, e.g., activate or inhibit, one or more complement pathways.

"Biological sample" refers to a sample that contains or consists of material obtained or derived from an organism, typically a living organism that has a complement system, e.g., a mammal, e.g., a human, non-human primate, rodent (e.g., mouse, rabbit, rat), dog, cat, or other domesticated animal or bird, etc. A biological sample can comprise, for example, any of the following: whole blood, fractionated blood, plasma, serum, other blood fraction or blood product, aqueous humor, vitreous humor, tears, synovial fluid, cerebrospinal fluid, saliva, mucous, sweat, milk, amniotic fluid, genital fluid, urine, fecal material, ascites fluid, pericardial fluid, gastric fluid, peritoneal fluid, pleural fluid, cyst fluid, broncheolar lavage fluid, nasal lavage, lymphatic fluid, mammary fluid, duct fluid, bone marrow, tears, prostatic fluid, tissue extract, glandular secretion, tissue extract, whole cell lysate or fraction thereof, cell or tissue extract, tissue homogenate, or cell culture supernatant. In some embodiments a biological sample is essentially cell-free. In some embodiments a biological sample contains no more than 1% cells by weight or volume. The term "biological sample" can also refer to a sample derived by processing a biological sample comprising any of the afore-mentioned materials, e.g., by fractionating or diluting the sample, isolating or purifying one or more substances (e.g., proteins) from the sample, etc.

"Detectable label" refers to a moiety that facilitates the direct or indirect detection and/or quantitative or relative measurement of a molecule to which it is attached. A detectable label often has a property such as fluorescence, chemiluminescence, radioactivity, color, magnetic or paramagnetic properties, etc., that renders it detectable, e.g., by the use of instruments that detect fluorescence, chemiluminescence, radioactivity, color, magnetic field, magnetic resonance, etc., or in some cases by visual inspection. The label may be, e.g., fluorescent substance; pigment; chemiluminescent or luminescent substance; colored substance; magnetic substance; or a non-magnetic metal particle such as gold colloid; a radioactive substance such as I-125, I-131, P-32, H-3, S-25, or C-14. A fluorescent or chemiluminescent label may be a fluorescein or a derivative thereof such as fluorescein isothiocyanate; rhodamine or a rhodamine derivative such as rhodamine isothiocyanate or tetramethyl rhodamine isothiocyanate; a dancyl chloride (5-(dimethylamino)-1-naphthalenesulfonyl chloride); a dancyl fluoride; a fluorescamine (4-phenylspiro[furan-2(3H); 1-(3H)-isobenzofuran]-3; 3-dione); a phycobiliprotein such as a phycocyanine or phycoerythrin; an acridinium salt; a luminal, lumiferin, luciferase, or aequorin; an imidazole; an oxalic acid ester; a chelate compound of a rare earth element such as europium (Eu), terbium (Tb) or samarium (Sm); or coumarin or a derivative thereof such as 7-amino-4-methylcoumarin. Other examples include derivatives of the phorphyrins, anthraquinones, anthrapyrazoles, perylenequinones, xanthenes, cyanines, acridines, phenoxazines and phenothiazines. In other embodiments the detectable label is a quantum dot. In some embodiments a detectable label may comprise an enzyme that acts on a substrate to produce a detectable substance. The enzyme may be a dehydrogenase; an oxidoreductase such as a reductase or oxidase; a transferase that catalyzes the transfer of functional groups, such as an amino; carboxyl, methyl, acyl, or phosphate group; a hydrolase that may hydrolyzes a bond such as ester, glycoside, ether, or peptide bond; a lyases; an isomerase; or a ligase. Examples include horseradish peroxidase, acid or alkaline phosphatase, etc. The enzyme may also be conjugated to another enzyme. The enzyme acts on a suitable substrate to produce a detectable substance. For example, para-Nitrophenylphosphate (pNPP) is a chromogenic substrate for acid and alkaline phosphatase. When the detectable label is an alkaline phosphatase, a suitable substrate may be an umbelliferone derivative, e.g., 4-methylumbellipheryl phosphate. Tetramethyl benzidine (TMB) is a substrate for horseradish peroxidase. In some embodiments the label may be a hapten, such as adamantine, biotin, or carbazole. The hapten may allow the formation of an aggregate when contacted with a multi-valent antibody or (strep) avidin containing moiety. The hapten may also allow easy attachment of a molecule to which it is attached to a solid substrate.

"Detecting" or "detection" refer to determining the presence of an analyte and often include providing a quantitative indication of the concentration or amount of the analyte.

"Epitope" refers to the minimum portion of a molecule that is recognized by, and thus determines the immunospecificity of, an antibody that binds to such epitope. The term is also used herein to refer to the minimum portion of a molecule that is recognized by a non-antibody specific binding agent. Unless otherwise indicated, it is assumed herein that a specific binding agent that binds to a complement protein binds to an epitope present and accessible for binding in the native protein, i.e., the epitope is not a neoepitope. In some embodiments the epitope does not undergo substantial structural change upon cleavage of a full length protein, so that it retains the ability to be bound by a specific binding agent that binds to the native protein. In some embodiments the affinity of such binding is not substantially affected by cleavage. For example, in some embodiments a specific binding agent binds to a C3d epitope that does not undergo substantial structural change upon cleavage of C3, C3b, iC3b, and/or C3dg.

"Isolated" means 1) separated from at least some of the components with which it is usually associated in nature; 2) prepared or purified by a process that involves the hand of man; and/or 3) not occurring in nature.

Two or more moieties are "linked" if they are physically associated or connected with one another to form a molecular structure that is sufficiently stable so that they remain associated under the conditions in which the linkage is formed and, preferably, under the conditions in which the molecular structure thus formed is used. In certain embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linker" or "linking moiety" or "linking portion", the linkage between the two linked moieties is indirect, and typically each of the linked moieties is covalently bonded to the linker. The linker can be any suitable moiety that reacts with the two moieties to be linked within a reasonable period of time, under conditions consistent with stability of the moieties (which may be protected as appropriate, depending upon the conditions), and in sufficient amount, to produce a reasonable yield.

"Matrix" as used herein, refers to a substance that contains complement component(s) or cleavage product(s) to be detected. A matrix can comprise any of the substance(s) listed above in the definition of "biological sample". A matrix can comprise any fluid in which proteins can be dissolved or suspended. Often a matrix comprises an aqueous medium.

"Neoepitope" is used herein as in the art to refer to an epitope that is generated or becomes detectable as a result of proteolytic cleavage of a complement component or cleavage product.

"Plurality" means more than one.

"Polypeptide", as used herein, refers to a polymer of amino acids, optionally including one or more amino acid analogs. A protein is a molecule composed of one or more polypeptides. A peptide is a relatively short polypeptide, typically between about 2 and 60 amino acids in length, e.g., between 8 and 40 amino acids in length. The terms "protein", "polypeptide", and "peptide" may be used interchangeably. Polypeptides used herein may contain amino acids such as those that are naturally found in proteins, amino acids that are not naturally found in proteins, and/or amino acid analogs that are not amino acids. As used herein, an "analog" of an amino acid may be a different amino acid that structurally resembles the amino acid or a compound other than an amino acid that structurally resembles the amino acid. A large number of art-recognized analogs of the 20 amino acids commonly found in proteins (the "standard" amino acids) are known. One or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. Certain non-limiting suitable analogs and modifications are described in PCT publications WO2004026328 and WO2007062249. The polypeptide may be acetylated, e.g., at the N-terminus and/or amidated, e.g., at the C-terminus The modifications can occur anywhere in a polypeptide, including the peptide backbone, the amino acid side-chains and the amino or carboxyl termini. A given polypeptide may contain many types of modifications. Polypeptides may be branched and/or cyclic, with or without branching. Polypeptides may, for example, be purified from natural sources, produced in vitro or in vivo in suitable expression systems using recombinant DNA technology in suitable expression systems (e.g., by recombinant host cells or in transgenic animals or plants), synthesized through chemical means such as conventional solid phase peptide synthesis and/or methods involving chemical ligation of synthesized peptides (see, e.g., Kent, S., *J Pept Sci.*, 9(9):574-93, 2003), or any combination of the foregoing.

"Reactive functional groups" as used herein refers to groups such as, but not limited to, olefins, acetylenes, alcohols, phenols, ethers, oxides, halides, aldehydes, ketones, carboxyl groups, hydroxyl groups, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those frequently used to prepare bioconjugates, e.g., N-hydroxysuccinimide esters, maleimides, sulfhydryls, and the like (see, for example, Hermanson, G., *Bioconjugate Techniques*, Academic press, San Diego, 1996). Methods to prepare each of these functional groups are well known in the art and their application to or modification for a particular purpose is within the ability of one of skill in the art (see, for example, Sandler and Karo, eds., "Organic Functional Group Preparations", Academic Press, San Diego, 1989).

A first molecule is said to "specifically bind" to a second molecule if it binds to the second molecule with substantially greater affinity than to most or all other molecules present and/or if the two molecules bind with an equilibrium dissociation constant, $K_d$, of $10^{-4}$ M or less, e.g., $10^{-5}$ M or less, e.g., $10^{-6}$ M or less, $10^{-7}$ M or less, $10^{-8}$ M or less, or $10^{-9}$ M or less under the conditions used. It will be understood that if a first molecule binds specifically to a particular epitope within a second molecule it may also bind specifically to other molecules that contain the same epitope, e.g., fragments of the second molecule that contain the epitope or larger molecules that contain the second molecule.

"Specific binding agent" refers to a molecule or molecular complex that specifically binds to a second molecule or molecular complex. The second molecule or molecular complex is sometimes referred to as a "target".

"Specific binding pair" refers to two molecules that specifically bind to one another. Examples are biotin-avidin, antibody-antigen, complementary nucleic acids, receptor-ligand, etc.

"Subject", as used herein, refers to an individual from whom a biological sample is obtained and/or on whom a test is performed or to whom an agent is administered or on whom a test is performed, e.g., for experimental, diagnostic, and/or therapeutic purposes. Unless otherwise indicated, subjects are mammals, e.g., humans, non-human primates, domesticated mammals such as dogs, or cats, rodents, such as rabbits, mice, etc. Typically the subject is human.

"Support" refers to any type of solid or semisolid physical structure or group of structures to which a binding agent can be attached. Typically a support has a rigid or semi-rigid surface or surfaces. In some embodiments at least one surface of the support is substantially planar while in other embodiments the surface is curved or irregular. Exemplary supports can be plates, e.g., microtiter plates (sometimes called multiwell plates), having, e.g., 96, 384, or 1536 wells, tubes (e.g., microfuge tubes), dishes, slides, filters, fibers, wires, rods, pins, slides, etc. In many embodiments, it may be desirable to analyze multiple aliquots of a sample, or multiple samples, in physically separated regions such as in individual wells.

A support can be made out of a wide variety of organic or inorganic materials or mixtures thereof and can have a variety of different shapes and sizes. Exemplary materials that may be used in the manufacture of suitable supports are polymeric materials, e.g., plastics, such as polypropylene, polystyrene, poly(meth)acrylates, polybutadienes, and the like, individually or in the form of copolymers or blends. Exemplary inorganic support materials are silicon oxide, silicon, mica, glass, quartz, titanium oxide, vanadium oxide, metals such as gold or silver, alloys such as steel, etc. A support can comprise a plurality of particles, often referred to as beads, resins, microspheres, or other geometric configurations. Particles may be microscopic or macroscopic and can have a variety of different shapes, e.g., spheres, spheroids, ellipsoids, etc. In some embodiments the particles average between about 20 nm and about 20 microns in diameter (or longest axis or other relevant dimension). In some embodiments the density of the particles is about 0.5 mg/ml to about 2.0 mg/ml. Particles may be made of a variety of materials, e.g., organic polymers (e.g., polystyrene), agarose, metals, etc., and may be homogeneous or heterogeneous in composition. The particles may be non-magnetic or magnetic. The term "magnetic" encompasses ferrimagnetic, ferromagnetic, paramagnetic, and superparamagnetic materials. Magnetic particles may comprise one or more materials selected from the group consisting of: iron, cobalt, nickel, niobium, magnetic iron oxides, iron hydroxides, and mixtures of any of the foregoing. Often magnetic particles comprise smaller particles of a magnetic material embedded in or encapsulated in a polymer material. Magnetic particles may be conveniently recovered from an assay composition by applying a suitable magnetic field, e.g., using a magnet, as known in the art. The particle surface may be functionalized with a moiety that comprises a reactive functional group or specific binding pair member so as to facilitate binding or attachment, either directly or indirectly, of a specific binding agent to the particle.

II. Assays for Intact C3, IC3B, Total C3, or Complement Activation

The present invention provides compositions, methods, and kits of use to assess the level of intact complement component C3 in a sample. The invention also provides compositions, methods, and kits of use to assess the level of iC3b or total C3 in a sample. In some aspects, the invention provides compositions, methods, and kits of use to assess complement activation. The invention also provides methods of diagnosing or monitoring subjects at risk of or suffering from complement-mediated disorders or conditions or complement deficiencies using an inventive assay described herein. Certain of the methods comprise assessing the level of intact C3 in a sample comprising serum, plasma, or blood obtained from the subject. The invention further provides methods of selecting appropriate therapy for a subject based at least in part on results of an inventive complement activation assay or an inventive assay for intact C3 described herein. Surprisingly, it was found that serum levels of intact C3 can be used to distinguish individuals with age-related macular degeneration (AMD), from individuals not having AMD. Individuals who had been diagnosed AMD were found to have significantly higher levels of intact C3 in their serum than individuals not having AMD (see Example 11). Accordingly, in some aspects, the invention provides methods of assessing a subject who has or may develop age-related macular degeneration (AMD). The invention also provides methods for deciding whether or when to administer therapy to a subject suffering from or at risk of developing AMD.

Certain aspects of the present invention are based at least in part on measuring the level of intact complement component 3 (C3). Certain aspects of the present invention are based at least in part on measuring activation of C3. C3 is the central protein of the complement system. C3 is synthesized as a single polypeptide chain. After removal of its signal sequence the pro-C3 polypeptide is post-translationally modified by proteolytic cleavage into two polypeptides (alpha and beta chains) linked by a disulfide bond to yield mature C3. This form of C3 is referred to herein as "intact C3" (FIG. 1a). The term "intact C3" is used interchangeably herein with "full length C3", "native C3", "uncleaved C3", "unactivated C3", or "unreacted C3". It will be appreciated that the term "native C3" is sometimes reserved for intact C3 molecules that have not undergone the first step of alternative pathway activation, i.e., hydrolysis of the thioester bond (or in which the thioester bond has reformed) and does not include the resulting conformational intermediate or the form into which this intermediate can be converted by an irreversible conformational transition (Nishida, N., et al. Proc. Natl. Acad. Sci. 103(52): 19737-42, 2006). However, in most embodiments of this invention, these forms of mature C3 are detected together with uncleaved C3, so the term "native C3" will be considered equivalent to "uncleaved C3" unless otherwise indicated. During complement activation intact C3 is cleaved by C3 convertase, releasing the C3a fragment (77 amino acids in humans) and the much larger C3b fragment (294 amino acids in humans) (FIG. 1b). See, e.g., Paul, W., supra and Nishida N, et al, Proc. Natl. Acad. Sci. 103(52):19737-42, 2006. C3b is normally rapidly cleaved and inactivated in vivo to the proteolytically inactive iC3b, releasing the small fragment C3f (FIG. 1c). iC3b is subsequently cleaved to form C3dg and C3c (FIG. 1d). Finally, C3dg is cleaved, giving rise to C3d and the much smaller fragment C3g (FIG. 1e). For purposes of the invention the terms "cleavage product", "split product", or the like refer to the specific, named complement protein fragments known in the art, a number of which are discussed herein (e.g., C3a, C3b, iC3b, C3dg, C3d, C3f, C3g, C4a, C4b, C5a, C5b).

The inventive approach, in certain embodiments, involves detecting intact C3. In some embodiments, an inventive method involves detecting intact C3 and detecting one or more C3 cleavage products. In most embodiments, "detecting" comprises quantifying the concentration or amount of the protein(s) detected, e.g., intact C3. Complement activation results in a reduced amount of, e.g., intact C3. In some aspects, complement activation results in increasing the level of C3 cleavage products. If little or no complement activation has occurred, the amounts of C3b and iC3b are low. Complement activation results in increased conversion of C3 to C3b, which is subsequently cleaved to yield iC3b. In certain embodiments of the invention, the extent of complement activation is determined at least in part by measuring the amount of iC3b, with a greater amount of iC3b indicating a greater extent of complement activation. In certain embodiments of the invention, the amount of intact C3 is also measured, and the ratio of iC3b to intact C3 is used as an indicator of the extent to which complement activation has occurred. If little or no complement activation has occurred, the amount of iC3b, and the amount of iC3b relative to intact C3, measured in a sample will be lower than if extensive complement activation has occurred. Thus a higher ratio of iC3b to intact C3 is indicative of greater complement activation than a lower ratio. In certain embodiments of the invention, the amount of total C3 is measured, and the ratio of iC3b to total C3 is used as an indicator of the extent to which complement activation has occurred, with a higher ratio of iC3b to total C3 being indicative of greater complement activation than a lower ratio. It will be appreciated that a ratio, e.g., a ratio of iC3b to intact C3, can be expressed in a variety of ways. For example, a ratio can be expressed as a number (which may be greater than, equal to, or less than 1), fraction, or quotient (e.g., concentration of iC3b divided by concentration of intact C3), or as otherwise known in the art. It will also be appreciated that determining a ratio of two values provides a determination of the reciprocal of the ratio. For purposes of the present invention "determining the ratio of iC3b to intact C3" encompasses determining any ratio or value that provides the relative amounts or concentrations of iC3b and intact C3, and "determining the ratio of iC3b to total C3" encompasses determining any ratio or value that provides the relative amounts or concentrations of iC3b and total C3.

It was found that certain complement component(s) and cleavage product(s) can give different signals when measured in different matrices and that various matrices themselves can interfere with detection. In certain embodiments the inventive methods produce accurate results when used to detect intact C3 or iC3b in samples comprising different biologically relevant matrices. In certain embodiments the inventive methods produce accurate results when used to detect complement activation in samples comprising different biologically relevant matrices. In certain embodiments the inventive methods are highly specific for detecting intact C3 versus C3b, iC3b, or C3d. In certain embodiments the inventive methods show superior reproducibility and the results exhibit less variation between individual users and between tests performed on the same sample on different days than is the case for a variety of commercially available and published assays for complement activation and/or for a complement component or cleavage product. In certain embodiments the inventive methods provide more consistent results when complement activation and/or a complement component or cleavage product is measured in different matrices, e.g., phosphate buffered saline (PBS), serum, vitreous, or blocking buffer, than is the case for a variety of commercially available and published assays for complement activation.

According to certain embodiments of the invention, the magnitude of the difference between the amounts of total C3 and intact C3 provides an indication of the extent to which complement activation has occurred. "Total C3" encompasses C3 present collectively in the five states shown in FIGS. 1b-1e. In some embodiments, detecting total C3 comprises detecting intact C3 and those cleavage products of C3 that comprise C3d. In these embodiments detecting total C3 comprises full length C3, C3b, iC3b C3dg, and C3d but does not comprise detecting C3a, C3c, C3f, and C3g as individual fragments. Detecting full length C3, C3b, and iC3b accounts for C3 molecules in states shown in FIGS. 1a-1c, while detecting C3dg and C3d accounts for C3 molecules in states 1d and 1e, respectively. In some embodiments, detecting total C3 comprises intact C3 and detecting those cleavage products of C3 that comprise C3c. In these embodiments detecting total C3 comprises full length C3, C3b, iC3b, and C3c but does not comprise C3a, C3d, C3dg, C3f, or C3g as individual fragments. Detecting full length C3, C3b, and iC3b accounts for C3 molecules in states shown in FIGS. 1a-1c, while detecting C3c accounts for C3 molecules in states 1d and 1e. If little or no complement activation has occurred, the amounts of intact C3 and total C3 in a sample are substantially identical, while if extensive complement activation has taken place, the amount of intact C3 will be much lower than that of total C3. For example, consider a sample that contains 100 unactivated C3 molecules and sufficient amounts of the upstream complement components. At time t=0 a complement activating agent is added. Over time, complement activation occurs and molecules of intact C3 are cleaved and pass through states shown in FIGS. 1b-1e. For example, at t=5, there might be 50 intact C3 molecules, 25 molecules in state 1b, 20 in state 1c, and 5 in state 1d, at which point it may be said that 50% complement activation has occurred. At t=10, there might be 25 intact C3 molecules, 25 molecules in state 1b, 20 molecules in state 1c, and 15 molecules in each of states 1d and 1f, at which point it may be said that 75% complement activation has occurred. Eventually all C3 molecules will have been cleaved, at which point it may be said that 100% complement activation has occurred. Of course in a living subject, ongoing synthesis of C3 may occur, and the results of an inventive assay may reflect the consequences of both synthesis and consumption.

Amounts (i.e., levels) of intact C3, iC3b, and/or total C3 are typically expressed in terms of concentration but may be expressed in terms of mass or weight. Concentration may be expressed in various ways, e.g., in terms of molarity, molality, mole fraction, mass fraction (mass of a substance in a mixture as a fraction of the mass of the entire mixture), mass per unit volume, etc. For purposes of description herein, concentration (e.g., mass per unit volume) will generally be used. One of skill in the art can readily convert between concentration and moles or mass in a given volume. The difference between the concentration of total and intact C3 may be expressed in a variety of ways. In some embodiments of the invention the difference is expressed in terms of relative concentrations. For example, the difference between the concentration of total C3 and intact C3 may be expressed as the fraction of C3 that is intact, e.g., concentration of intact C3 divided by concentration of total C3 (which may be multiplied by 100 to obtain a percentage), or as the ratio of the concentration of total C3 to the concentration of intact C3 or vice versa. In some embodiments, the difference is expressed as an absolute number.

It will be appreciated that an initial sample (e.g., a sample obtained from a subject) may be divided into multiple smaller samples, which are also considered "samples" but may at times be referred to as sub-samples, or aliquots. In some embodiments, a measurement is performed on multiple aliquots and the results are averaged. For example, in some embodiments, intact C3 is measured in more than one aliquot, and the results are averaged to determine an intact C3 value for the sample. In some embodiments, iC3b is measured in more than one aliquot and the results are averaged to determine an iC3b value for the sample. The ratio of the averages is then obtained in those embodiments of the invention that involve determining the ratio of iC3b to intact C3. In some embodiments, total C3 is measured in more than one aliquot, and the results are averaged.

Biological samples may be diluted so that the analytes are present in a suitable concentration to be accurately quantified. In some embodiments a sample is diluted with an aqueous medium. In some embodiments a sample is diluted with a blocking buffer. In some embodiments the blocking buffer is a standard blocking buffer useful in an ELISA assay to reduce non-specific binding of detection antibodies. In some embodiments the blocking buffer is a protein-free blocking buffer, e.g., cat. no. 37570, 37571 37572, or 37573 from Thermo Fisher Scientific, Inc. In some embodiments the blocking buffer comprises one or more proteins. In most embodiments the blocking buffer is free of C3 and C3 cleavage fragments. In some embodiments a sample is diluted with phosphate buffered saline or tris buffered saline. In some embodiments, a blood, plasma, or serum sample is diluted so that it contains no more than 0.5%, no more than 0.25%, no more than 0.1%, or no more than 0.05% blood, plasma, or serum, respectively. In some embodiments, a sample contains up to 0.5%, up to 0.25%, up to 0.1%, or up to 0.05% blood, plasma, or serum. In some embodiments, a vitreous or aqueous humor sample is diluted so that it contains no more than 40%, no more than 30%, no more than 20%, or no more than 10% vitreous or aqueous humor. In some embodiments, a sample contains up to 40%, up to 30%, up to 20%, or up to 10% vitreous or aqueous humor.

In some embodiments, to obtain a sample, blood may be drawn directly into tubes containing EDTA at a final concentration of at least about 10 mM. In some embodiments, one or more protease inhibitors are added to the samples or to the assay composition. In some embodiments a complement inhibitor is added to the sample to inhibit complement activation. In some embodiments a sample is processed to remove one or more abundant proteins prior to assessing levels of intact C3. For example, it may be desirable to remove one or more abundant proteins selected from the group consisting of: albumin, fibrinogen, transferrin, IgA, IgM, IgG, α2-macroglobulin, α1-antitrypsin, haptoglobin, apo A-I, apo A-II, LDL (ApoB), α1-acid glycoprotein, vitronectin, α-crystallin and/or β-crystallin from a blood, plasma, serum, vitreous humor, aqueous humor, or CSF sample. Such depletion can be accomplished, e.g., using immunoaffinity approaches in which a sample is contacted with antibodies to the protein(s) whose removal is desired. For example, Seppro® columns, microbeads, and tips (available from Sigma-Aldrich) comprise chicken IgY antibodies immobilized on a support and provide a convenient means to remove one or more such proteins from a sample.

A variety of methods may be used to detect intact C3, iC3b, and/or total C3. In many embodiments, the methods for detecting intact C3 comprise (a) providing a sample; (b) providing a specific binding agent that binds to intact C3; and (c) detecting binding of the specific binding agent to analyte(s) present in the sample. In many embodiments, the methods for detecting intact iC3b comprise (a) providing a sample; (b) providing a specific binding agent that binds to iC3b and substantially does not bind to intact C3 or to C3b; and (c) detecting binding of the specific binding agent to analyte(s) present in the sample. In many embodiments, binding is detected in a quantitative manner, thereby providing an indication of the amount of intact C3 or iC3b, respectively, present in the sample. In some embodiments, the methods for detecting total C3 comprise (a) providing a sample; (b) providing a specific binding agent that binds to full length C3 and to cleavage products that contain C3d; and (c) detecting binding of the specific binding agent to analyte(s) present in the sample. In some embodiments, binding is detected in a quantitative manner, thereby providing an indication of the amount of intact C3, iC3b, or total C3 present in the sample. The phrase "specific binding agent that binds to intact C3" is intended to indicate that the specific binding agent binds to intact C3 and may bind to C3a but does not bind to other C3 cleavage products. For example, an antibody that binds to an epitope within C3a (such epitope not being a neo-epitope) is considered a specific binding agent that binds to intact C3, since intact C3 comprises C3a. Such an agent would not, however, bind to C3c, C3b, C3dg, or cleavage products thereof. A binding agent that specifically binds to a particular complement component will in many cases also bind to one or more cleavage products of the component. For example, a monoclonal antibody that binds to an epitope of C3 may bind most or all C3 cleavage products that contain the epitope. A binding agent that specifically binds to a cleavage product of interest will in many cases also bind to products obtained by further cleavage of the cleavage product of interest as well as to the full length complement component that comprises the cleavage product of interest and any larger cleavage products that comprise the cleavage product of interest. A specific binding agent that binds to iC3b but substantially does not bind to intact C3 or C3b may bind to at least some cleavage products of iC3b, e.g., C3d. In certain embodiments of the invention a specific binding agent that binds to a first analyte is said to "not substantially bind" to a second analyte if one or more of the following conditions is/are met: (i) a sample that contains equal concentrations X of the first analyte and the second analyte produces no more than 1.25 times as large a signal, or in some embodiments no more than 1.1 times as large a signal, or in some embodiments no more than 1.05 times as large a signal, as does a sample that contains only the first analyte at concentration X when the specific binding agent is used as a capture agent to quantitate analyte(s) in the sample (assuming that the detection agent used is able to detect the first and second analytes with approximately equal efficiency or results are adjusted to account for varying detection efficiency); (ii) a sample that contains equal concentrations X of the first analyte and the second analyte produces no more than 1.25 times as large a signal, or in some embodiments no more than 1.1 times as large a signal, or in some embodiments no more than 1.05 times as large a signal, as does a sample that contains only the first analyte at concentration X when the specific binding agent is used as a detection agent to quantitate analyte(s) in the sample (assuming that the capture agent used is able to capture the first and second analytes with approximately equal efficiency or results are adjusted to account for varying capture efficiency); (iii) when the specific binding agent is used as a capture agent, a sample that contains a concentration X of the second analyte produces no more than 25% of the signal, or in some embodiments no more than 10% of the signal, or in some embodiments no more than 5% of the signal produced by a sample that contains the same concentration X of the first analyte (assuming that the detection agent used is able to detect the first and second analytes with approximately equal efficiency or results are adjusted to account for varying detection efficiency); (iv) when the specific binding agent is used as a detection agent, a sample that contains a concentration X of the second analyte produces no more than 25% of the signal, or in some embodiments no more than 10% of the signal, or in some embodiments no more than 5% of the signal produced by a sample that contains the same concentration X of the first analyte (assuming that the capture agent used is able to capture the first and second analytes with approximately equal efficiency or results are adjusted to account for varying capture efficiency). Specificity may be assessed over or an analyte concentration range of interest or a portion thereof (see Examples) and may be assessed using pure complement components or cleavage products, e.g., in a matrix similar to that in which binding would occur when the specific binding agent is used in an assay of the invention. Background signal from a sample containing the matrix alone (i.e., without added first or second analyte) may be subtracted.

Native complement proteins or cleavage products may be substrates for nonspecific proteases and/or other proteolytic or other breakdown pathways in addition to, or instead of, those that generate the cleavage products discussed herein. The term "degradation products" refers to complement protein fragments, e.g., C3 fragments, other than the characteristic cleavage products specifically mentioned herein. In some embodiments of the invention intact C3, iC3b or total C3 comprises at least some degradation products. Whether or not a particular degradation product is included within intact C3, iC3b, or total C3 in a given embodiment of the invention will often depend at least in part on the properties of the binding agent(s) used in that embodiment and is not expected to significantly affect the results of the assay.

A variety of specific binding agents are of use in various embodiments of the present invention. In many embodiments of the invention the specific binding agent(s) are antibodies. Antibodies can be monoclonal or polyclonal and can be prepared by techniques that are well known in the art. Briefly, such methods include (i) immunizing a host such as a rodent (mouse, rabbit, etc.), chicken, goat, sheep, cow, or other animal with an antigen of interest and collecting sera (for polyclonal antibodies); or (ii) preparing and culturing (in vivo or in vitro) an immortalized hybrid cell line wherein one of the cells produces an antibody of interest (obtained from a host such as a mouse that has been immunized with or otherwise exposed to an antigen of interest) and the other cell is a myeloma cell and collecting the secreted protein (for monoclonal antibodies). It will be appreciated that antibodies may be collected from chicken eggs, milk, transgenic animals or plants engineered to express an immunoglobulin, etc. In some embodiments a host is immunized with a nucleic acid construct or virus that encodes the antigen of interest. Antibodies (usually monoclonal) can also be generated by cloning and expressing nucleotide sequences or mutagenized versions thereof that encode at least the amino acid sequences of an antibody required for specific binding or by chemical synthesis (see, e.g., Allen, T., Nature Reviews Cancer, Vol. 2, 750-765, 2002, and references therein). Such amino acid sequences may be obtained from an antibody originally produced by a host or may be generated and/or selected in vitro using techniques such as phage display (Winter, G. et al., Annu. Rev. Immunol. 12:433-455, 1994), ribosome display (Hanes, J., and Pluckthun, A. Proc. Natl. Acad. Sci. USA. 94:4937-4942, 1997), etc. To prepare antibodies for use in the present invention, complement components (e.g., full length C3) or cleavage products (e.g., C3a, C3d, etc.) may be used as antigens. Such proteins may be purified from serum or produced recombinantly or by chemical synthesis. In some embodiments a full length protein is used as an antigen while in other embodiments a portion is used, e.g., a portion generated by cleaving a full length component in vitro or in vivo. Peptides (usually at least 8-10 amino acids in length, e.g., between 8 and 50 amino acids, and usually produced by chemical synthesis) whose sequence is derived from that of a larger polypeptide may be used and can be particularly useful if it is desired to generate an antibody that binds to a particular region of a polypeptide. The antigen may be conjugated to a carrier or otherwise modified prior to immunizing the host. Antibodies may be purified from sera, ascites fluid, or cell culture supernatant, etc., using well known methods such as affinity purification, e.g., protein A/G affinity purification and/or affinity purification using the antigen as an affinity reagent. See, e.g., Kaser, M. and Howard, G., "Making and Using Antibodies: A Practical Handbook" and Sidhu, S., "Phage Display in Biotechnology and Drug Discovery", CRC Press, Taylor and Francis Group, 2005.

A variety of non-immunoglobulin specific binding agents could be used in various embodiments of the invention. For example, anticalins are binding proteins that are constructed on the basis of lipocalins as a scaffold (Skerra, J., J. Biotechnol., 74(4):257-75, 2001). Affibodies are binding proteins generated from combinatorial libraries constructed using the protein A-derived Z domain as a scaffold (see, e.g., Nord K, Eur J. Biochem., 268(15):4269-77, 2001). Nucleic acid ligands, sometimes referred to as aptamers, are oligonucleotides that bind specifically and with high affinity to a target. They can comprise DNA, RNA, and/or non-standard nucleotides, e.g., 2'-fluoro or 2'-O-methyl modified nucleotides, and may be identified using, e.g., systematic evolution of ligands by exponential enrichment (SELEX) or various directed evolution techniques that are known in the art. See, e.g., Tuerk, C. and Gold, L., Science 249(4968): 505-10, 1990; Brody E N, Gold L. J. Biotechnol., 74(1):5-13, 2000. Aptamers that bind to C3 have been identified. See, e.g., U.S. Pat. Pub. No. 20030191084. The invention provides embodiments in which each type of specific binding agent described herein is employed.

In some embodiments of the invention an ELISA assay is used to detect intact C3, iC3b, and/or total C3. As used herein, the term "ELISA assay" refers to any of a number of techniques that may be used to detect the presence of an analyte of interest in a sample. In ELISA assays the analyte of interest is directly or indirectly immobilized on a support and is contacted with a first specific binding agent that binds to the analyte and a detection enzyme is used to detect the first specific binding agent. Suitable detection enzymes are known in the art, and a number are mentioned above. The detection enzyme is contacted with a substrate on which it acts to generate a detectable signal. For example, the substrate may be a chromogenic or fluorogenic substrate that generates a colored or fluorescent moiety, when acted on by the enzyme, e.g., when cleaved by the enzyme. The detection enzyme may be linked to the first specific binding agent. In many embodiments, however, the detection enzyme is linked, e.g., covalently linked, to a second specific binding agent that specifically binds to the first specific binding agent. In some embodiments, the detection enzyme is linked, e.g., covalently linked, to a third specific binding agent that binds to the second specific binding agent. For example, the second specific binding agent may be linked to biotin and the detection enzyme linked to avidin or steptavidin.

A number of different ELISA assay types may be used. These general assay formats are well known in the art. In a sandwich ELISA, a first specific binding agent that binds to the analyte is immobilized on a support and used to "capture" analyte present in the sample. The first specific binding agent may be referred to as a "capture agent". Analyte present in the sample binds to the first specific binding agent and is thereby immobilized. Unbound material may be removed. One or more washing steps may be perfomed. A composition comprising a second specific binding agent specific for the analyte is then contacted with the support. The second specific binding agent serves as a "primary detection agent" and binds to analyte that had been immobilized via binding to the first specific binding agent. Unbound second specific binding agent is typically removed. The second specific binding agent is then detected. In some embodiments the second specific binding agent has an enzyme linked thereto. In some embodiments the second specific binding agent does not have an enzyme linked thereto but instead is detected using a third specific binding agent ("secondary detection agent") that binds to the second specific binding agent and has an enzyme linked thereto. In some embodiments the primary detection agent comprises an antibody and the secondary detection agent comprises an antibody that binds to the antibody of the primary detection agent (e.g., to the Fc domain). It will be appreciated that in such cases it may be desirable to avoid using capture agent and primary detection agent that comprise antibodies raised in the same species in order to avoid the secondary detection agent binding to the capture agent. In some embodiments the primary detection agent comprises an antibody linked to a first member of a specific binding pair, and the secondary detection agent comprises an antibody linked to the other member of the specific binding pair, thus enabling use of a secondary detection agent that does not bind to the antibody portion of the primary detection agent. For example, the primary detection agent may comprise an antibody to which biotin has been conjugated, and the secondary detection agent may comprise avidin or streptavidin conjugated to an enzyme or may comprise a preformed complex between avidin or streptavidin and a biotinylated enzyme. In another embodiment the primary detection agent comprises an antibody conjugated to biotin, and the secondary detection agent comprises avidin or streptavidin conjugated to an enzyme or comprises a complex between avidin or streptavidin and a biotinylated enzyme. Biotin/avidin and biotinistreptavidin are exemplary specific binding pairs and that others could be used in these embodiments.

Often the capture agent and the primary detection agent are different. For example, it may be desirable to select capture and primary detection agents that bind to different portions of an analyte to avoid binding by the capture agent from interfering with binding by the primary detection agent. In some embodiments, the capture agent is a monoclonal antibody that binds to an analyte (e.g., intact C3 or iC3b) and the primary detection agent is a polyclonal antibody that binds to the analyte. In some embodiments, the capture agent may be a polyclonal antibody that binds to an analyte and the primary detection agent may be a monoclonal antibody that binds to the analyte. The polyclonal antibody will typically contain a plurality of antibody molecules that bind to different epitopes of an antigen. Thus capturing an analyte using a monoclonal antibody is not expected to interfere with detection using a polyclonal antibody, and capturing an analyte using a polyclonal antibody is not expected to interfere with detection using a monoclonal antibody as a primary detection agent. In some embodiments the capture agent and the primary detection agent are monoclonal antibodies that bind to different epitopes of an analyte.

In some embodiments of particular interest a monoclonal antibody that specifically binds to the C3a portion of C3 and substantially does not bind to C3 fragments that do not contain C3a is used as a capture agent for intact C3. In some embodiments a monoclonal antibody that specifically binds to a neoepitope of iC3b and substantially does not bind to intact C3 or to C3b is used as a capture agent for iC3b. In these embodiments of the invention a polyclonal antibody that binds to C3 is often used as a detection agent. The polyclonal antibody must contain at least some antibody molecules that bind to iC3b. In some embodiments the anti-C3 polyclonal antibody is a goat antibody. In some embodiments the anti-C3 polyclonal antibody is a chicken antibody. In some embodiments horseradish peroxidase is conjugated to the antibody.

An aspect of certain embodiments of the invention is the selection of antibodies for use as capture and detection agents. The inventors discovered that many published and commercially available antibodies exhibited significant and unexpected crosstalk between intact C3 and various C3 cleavage products or between different C3 cleavage products. For example, certain monoclonal antibodies against human C3a show significant and unexpected cross-reactivity with C3b and iC3b. It was recognized that cross-reactivity could be a significant source of inaccuracy in certain situations. Of particular concern in developing an assay for iC3b was crosstalk between intact C3 and iC3b observed with many of the iC3b antibodies tested. Further testing showed that crosstalk between C3b and iC3b was even more significant with at least some of these antibodies. This was of concern because iC3b levels are expected to be present at much lower levels than intact C3 in patient samples. One aspect of certain embodiments of the invention is the selection of antibodies with specificity for intact C3 or iC3b so as to minimize such crosstalk.

In some embodiments of the invention, an antibody used to capture or detect intact C3 is characterized in, when used as a capture agent on samples that contain either intact C3, C3b, iC3b, C3c, or C3d at a concentration of about 0.67 µg/ml, followed by detection using an anti-C3 antibody (e.g., goat anti-C3-HRP antibody such as MP Biomedicals, cat. no. 55237), the signal from the sample containing intact C3 is at least 9-fold as great as the signal from samples containing either C3b, iC3b, C3c, or C3d. In some embodiments of the invention, an antibody used to capture or detect intact C3 is characterized in, when used as a capture agent on samples that contain either intact C3, C3b, iC3b, C3c, or C3d at a concentration of about 0.2 µg/ml, followed by detection using an anti-C3 antibody (e.g., goat anti-C3-HRP antibody such as MP Biomedicals, cat. no. 55237), the signal from the sample containing intact C3 is at least 15-fold as great as the signal from samples containing either C3b, iC3b, C3c, or C3d. In some embodiments, an antibody used to capture or detect intact C3 has approximately equal or greater ability to distinguish intact C3 from C3b, iC3b, C3c, and C3d in samples containing such proteins (e.g., at concentrations and under conditions described in the relevant Examples or Figures) as does anti-C3a monoclonal antibody clone 474 (cat. no. HM2073 Hycult Biotechnology, available from Cell Sciences, Inc., Canton, Mass.) or clone 2898 (cat. no. HM 2075, Hycult Biotechnology, available from Cell Sciences, Inc., Canton, Mass.) when used as a capture agent or detection agent, respectively. In some embodiments of the invention an antibody used to capture or detect intact C3 binds to the same epitope of C3a as does the mAb of clone 474 or clone 2898. A second mAb that binds to the same epitope as a first mAb may be identified, e.g., by screening a panel of mAbs raised against C3a to identify those that compete with the first mAb for binding to C3a. One can clone the genes encoding the heavy and light chains, or at least the complementarity determining regions (CDRs) or variable domains of the heavy and light chains from an antibody-producing cell clone. The heavy and light chain genes can then be expressed in a heterologous cell. The CDRs or variable domains, and optionally additional amino acids, can be "grafted" to a different antibody, e.g., can be used in place of the corresponding CDRs or variable domains of such antibody, resulting in an antibody with equivalent binding specificity.

In some embodiments of the invention, an antibody used to capture or detect iC3b is characterized in that, when used as a capture agent on samples that contain either iC3b, C3, or C3b at a concentration of 10 µg/ml, followed by detection using an anti-C3 antibody, the signal from the sample containing iC3b is at least 5-fold as great as that from the samples containing C3 or C3b. In some embodiments of the invention, an antibody used to capture or detect iC3b is characterized in that, when used as a capture agent on samples that contain either iC3b, C3, or C3b at a concentration of 5 µg/ml, followed by detection using an anti-C3 antibody, the signal from the sample containing iC3b is at least 7.5-fold as great as that from the samples containing C3 or C3b. In some embodiments of the invention, an antibody used to capture or detect iC3b is characterized in that, when used as a capture agent on samples that contain either iC3b, C3, or C3b at a concentration of 2.5 µg/ml, followed by detection using an anti-C3 antibody, the signal from the sample containing iC3b is at least 15-fold as great as that from the samples containing C3 or C3b. In some embodiments, an antibody used to capture or detect iC3b has approximately equal or greater ability to distinguish iC3b from intact C3 and from C3b in samples containing such proteins (e.g., at concentrations and under conditions described in the relevant Examples or Figures) as does anti-iC3b antibody catalog A209 (Quidel Corp., San Diego, Calif.) (Tamerius, J. D., M. Pangburn, et al., Detection of a neoantigen on human iC3b and C3d by monoclonal Antibody, J. Immunol. 135:2015, 1985) when used as a capture agent or detection agent, respectively. In some embodiments of the invention the antibody used to capture or detect iC3b binds to the same epitope of iC3b as does mAb A209.

In some embodiments of the invention a polyclonal antibody that specifically binds to C3d (as well as to intact C3 and all cleavage products that contain C3d) is used as a capture or detection agent for intact C3, iC3b, and/or total C3. In some embodiments of the invention a polyclonal antibody that specifically binds to C3 (and to all cleavage products that contain C3d or C3c) is used as a capture agent or detection agent for intact C3, iC3b, and/or total C3.

A variety of different peptides or C3 fragments could be used as antigens for purposes of producing a polyclonal or monoclonal antibody having desired binding properties, e.g., (i) binds to C3d as well as to intact C3 and all cleavage products that contain C3d; (ii) binds to intact C3 and all cleavage products that contain C3c; (iii) binds to intact C3 but not to C3 cleavage products that do not contain C3a; (iv) binds to iC3b but substantially does not bind to intact C3 or C3b. In some embodiments anantibody that binds to C3d is raised against an antigen that comprises or consists of C3d. In some embodiments anantibody that binds to C3d is raised against an antigen that comprises or consists of at least half of C3d. In some embodiments anantibody that binds to C3 is raised against an antigen that comprises or consists of full length C3. In some embodiments anantibody that binds to C3 is raised against an antigen that comprises or consists of a portion of C3 that comprises at least half of C3. In some embodiments the antibody that binds to intact C3 but not to C3 cleavage products that do not contain C3a is raised against an antigen that comprises or consists of C3a. In some embodiments an antibody that binds to iC3b but substantially does not bind to C3 or C3b is raised using iC3b or a portion thereof (e.g., a portion that contains a new terminus generated by cleavage of C3b) as an antigen. Antibodies can be screened to identify those with desired binding properties.

Exemplary antibodies of use in certain embodiments of the present invention are described in the Examples. In some embodiments, an antibody that binds to the same epitope as an antibody described in the Examples is used. One of skill in the art can screen panels of monoclonal antibodies to identify those that bind to the same epitope as another antibody. In some embodiments, an antibody that has similar binding affinity for its target as an antibody described in the Examples is used. Additional antibodies that specifically bind to complement components such as C3a, C3d, C3c, C3, etc., are commercially available.

In an indirect ELISA, the analyte is attached directly to the support, e.g., by adsorption. Often other substances present in the sample (e.g., other proteins) are also adsorbed. A first specific binding agent that serves as a primary detection agent is contacted with the support and binds to the analyte. Unbound specific binding agent is removed and the support is washed. In some embodiments the primary detection agent comprises a detection enzyme, which is contacted with a substrate to detect the analyte. Alternately a second specific binding agent that specifically binds to the first specific binding agent is contacted with the support and binds to the first specific binding agent. Unbound second specific binding agent is removed. The second specific binding agent has a detection enzyme linked thereto, which is used to detect the analyte. In other embodiments, the second specific binding agent does not comprise a detection enzyme. Instead, after allowing the second specific binding agent to bind to the primary detection agent, unbound second specific binding agent is removed and the support is then contacted with a third specific binding agent that binds to the second specific binding agent and has a detection enzyme linked thereto, which is used to detect the analyte.

In a competitive ELISA, a first specific binding agent that recognizes the analyte is contacted with a sample containing analyte. The resulting assay composition is maintained to allow formation of binding agent/analyte complexes. The assay composition is then contacted with a support that has analyte attached thereto. Specific binding agent that is not in a complex with the analyte in the assay composition binds to analyte attached to the support. Unbound specific binding agent is then removed. Binding agent that remains bound to the support is then detected using a second binding agent to which an enzyme is bound. A substrate is added, and the enzyme acts on the substrate to generate a detectable signal. In this type of ELISA assay, the higher the analyte concentration, the weaker the resulting signal.

While ELISA assays are of particular interest herein, other methods of detecting intact C3, iC3b, and/or total C3 may be used in certain embodiments of the invention. Many of these assays are similar to ELISA assays in that they involve detecting an analyte that has been immobilized on a support but use a detectable label that is not an enzyme. For example, a specific binding agent used for detection purposes may be labeled with a detectable label other than an enzyme, e.g., a fluorescent or chemiluminescent substance such as fluorescein, rhodamine, phycoerythrin, a quantum dot, etc. For purposes of description the term "ELISA assay" should be understood to encompass embodiments in which such non-enzyme detectable labels are used.

ELISA assays may be performed in a variety of ways depending at least in part on the nature of the support. For example, an analyte or capture agent may be immobilized on the surface of a receptacle such as a well of a multiwell plate, e.g., by adsorption or via a reactive functional group. Reagents are added to the well in a sequence of steps separated by washing steps in which unbound reagents are removed. Alternately, reagents can be placed in different receptacles and an analyte or capture agent immobilized on a surface that can be transferred from one receptacle to another, with washing steps between transfers. For example, the analyte could be immobilized on a rod or pin, which is dipped sequentially into a receptacle containing a first specific binding agent, a receptacle containing a second specific binding agent that binds to the first specific binding agent, and then a receptacle containing an enzyme substrate (with wash steps in between). In another embodiment the capture agent is immobilized on a rod or pin which is dipped into a receptacle containing a sample and then sequentially into a receptacle containing a second specific binding agent, and a receptacle containing an enzyme substrate (with wash steps in between).

In some embodiment a particle-based ELISA is used. Suitable particles for use in performing biological assays, e.g., immunoassays, are known in the art and are commercially available from, e.g., Promega, Inc. (Madison, Wis.), Sigma-Aldrich (St. Louis, Mo.), Magsphere, Inc. (Pasadena, Calif.), Dynal (now part of Life Technologies, Carlsbad, Calif.). In one embodiment, magnetic beads are retained in a receptacle using a magnetic force while reagents are sequentially added to the receptacle and removed. In one embodiment, a particle-based ELISA assay uses spectrally discrete polystyrene beads to immobilize the capture antibody (or other capture agent). For example, carboxy-coated microspheres internally labeled with two fluorescent dyes that produce up to 100 different spectral addresses available from Bio-Rad Laboratories, Inc. (Hercules, Calif.) may be used. Similar to some traditional sandwich ELISA assays, each antibody-coupled bead captures analytes that are detected with a biotinylated antibody and phycoerythrin-conjugated streptavidin (SA-PE). For each capture antibody-coupled bead, the reader simultaneously measures the fluorescent signals of the bead's particular spectral address and of the SA-PE. Each mean fluorescence intensity reading corresponds to the average of the fluorescent signals from many (e.g., hundreds to thousands) of antibody-coupled beads having a particular spectral address. In the absence of cross-reactivity, each reading can assess the concentration of multiple analytes that are detected by spectrally distinct beads. The Bio-Plex Multiplex Suspension Array System (Bio-rad) and Luminex's (Luminex; Austin, Tex.) flow cytometer with carboxylate xMap™ microspheres (also Luminex) are commercially available platforms that can be used to implement such assays. Specific binding agents might be selected that bind to any peptide, polypeptide, small molecule, or other analyte that is or may be present in a biological sample in which complement activation is to be assessed. Exemplary analytes include soluble complement regulatory proteins (e.g., CFH), coagulation factors and regulators, hormones, growth factors (e.g., vascular endothelial growth factor), acute phase proteins (e.g., C-reactive protein), cytokines, chemokines, cardiac markers (e.g., proteins that are elevated in individuals who have suffered a heart attack), cancer markers, etc.

In certain of the ELISA assays of the invention the capture agent may be immobilized on a support by any suitable means, provided that it remains capable of retaining the analyte following immobilization. For example, a capture agent may be immobilized by adsorption, covalent interaction, chelation, molecular recognition, etc. In some embodiments a capture agent is immobilized via a physical interaction between the capture agent and the support, while in other embodiments the capture agent and support each interact with a third entity that links the capture agent to the support. For example, in some embodiments a first member of a specific binding pair is linked to the support and a second member of the specific binding pair is linked to the capture agent. Binding of the members of the specific binding pair to each other immobilizes the capture agent. In yet other embodiments a bifunctional specific binding agent is used to attach the capture agent to the support. The bifunctional specific binding agent contains a first domain that links it to the support (or to a moiety that is linked to the support) and a second domain that links it to the capture agent (or to a moiety that is linked to the capture agent). In some embodiments, capture agents are immobilized on discrete spots on a support, e.g., within individual wells of a microtiter plate. For example, a microtiter plate in which a monoclonal antibody against C3 a or a monoclonal antibody against iC3b is adsorbed to individual wells may be used to perform certain of the inventive assays. In other embodiments a polyclonal antibody against C3 or C3d is adsorbed to individual wells and may be used to perform certain of the inventive assays.

One of skill in the art will be aware that ELISA assays typically include additional steps not necessarily described in detail above, such as blocking, washing, preparing standard curves, etc. Further details are provided in the Examples and in references cited herein.

In some embodiments of the invention a standard curve for use with samples comprising a particular matrix (e.g., serum, plasma, vitreous, etc.) is prepared by "spiking" the matrix (which may be a diluted matrix) with purified analyte (e.g., intact C3 or iC3b) and measuring the signal obtained at different concentrations of analyte. The concentrations may embrace the range of concentrations that is desired to measure and/or that are expected to be present in samples of interest (e.g., after appropriate dilution). A background signal, e.g., the signal obtained from the matrix alone may be subtracted from each value when preparing the standard curve. The matrix used to generate the standard curve may be diluted, in which case the background value subtracted may be obtained at the same matrix dilution. For example, when preparing a standard curve for samples containing 0.1% serum, a background value due to 0.1% serum alone may be subtracted from the values obtained using 0.1% serum spiked with an analyte. When using the assay to measure complement activation on an actual sample comprising that matrix, a background value obtained from a sample of the diluent may be subtracted. Subtraction of the background signal from a diluent sample can help minimize the effect of non-specific binding of detection agent to the vessel or capture agent. In some embodiments, a standard curve for an analyte of interest is generated by spiking a matrix with the analyte of interest, wherein the matrix has been depleted of endogenous analyte.

In some embodiments of the invention the analyte is not immobilized on a support prior to binding of a detection agent to the analyte. For example, in some inventive assays an analyte of interest and a specific binding agent bind in solution to form a complex. Complexes containing the analyte and the specific binding agent are subsequently detected, e.g., using turbidometry or nephelometry. In some embodiments, complexes containing the analyte and the specific binding agent are immobilized on a support prior to detection. Unbound material is removed, and the support is optionally subjected to one or more washing steps to remove substances not bound to the specific binding agent.

In some embodiments a label-free detection method is used to detect intact C3, iC3b, and/or total C3. For example, capture of an analyte may be detected by detecting a change in mass, charge, piezoelectricity, bending, surface plasmon resonance, or other physical property, that occurs upon binding of the analyte to a capture agent immobilized on a support. For example, cantilever biosensors can be used (see, e.g., Fritz, J. Analyst, 133(7):855-63, 2008; Mutharasan, R., Methods Mol. Biol. 504:73-82, 2009). The same capture agents as described for ELISA assays may be used in these techniques. Other techniques that might be used in various embodiments of the invention include radioimmunoassay, immunodiffusion, nephelometry, electroimmunoassay, turbidometry, time-resolved immunofluoremetric assay, Western blot, immunoprecipitation, etc.

Without wishing to be bound by any theory, certain of the inventive assays may show superior accuracy and/or reproducibility relative to various other assays for complement and/or for complement activation. In some embodiments, superior results are achieved through use of a combination of selected capture and/or detection agents, standard curves generated using the same matrix as found in a biological sample of interest, and/or appropriate sample dilutions.

III. Kits and Assay Systems

The invention provides kits for use in performing one or more inventive assays. Certain of the kits comprise at least one specific binding agent that binds to intact C3. Certain of the kits comprise at least one specific binding agent that binds to iC3b. The kit may comprise any one or more of the specific binding agents described herein. For example, in some embodiments a kit comprises a polyclonal antibody that bind to C3 or C3d and a monoclonal antibody that binds to C3a. Such kits are of use, e.g., to determine the level of intact C3.

In some embodiments, a kit comprises at least one specific binding agent that binds to total C3 and at least one specific binding agent that binds to intact C3. In certain embodiments the kits comprise at least three specific binding agents, wherein one of the binding agents binds to a neoepitope of iC3b, one of the binding agents bind to total C3, and one of the binding agents binds to intact C3. In some embodiments a kit comprises a polyclonal antibody that bind to C3, a monoclonal antibody that binds to C3a, and a monoclonal antibody that binds to a neoepitope of iC3b. In some embodiments a kit comprises a polyclonal antibody that bind to C3d, a monoclonal antibody that binds to C3d, and a monoclonal antibody that binds to C3a. In some embodiments the kit comprises one or more receptacles, e.g., a microwell plate, comprising a surface having a specific binding agent covalently or noncovalently attached thereto, wherein the specific binding agent serves as a capture agent for intact C3, iC3b, or total C3. For example, the kit may comprise a microwell plate at least some of whose wells are at least partly coated with an antibody that binds to C3a, to C3d, to a neoepitope of iC3b, etc. In some embodiments the kit comprises one or more populations of particles having a specific binding agent attached thereto, wherein the specific binding agent serves as a capture agent for intact C3, iC3b, or total C3. For example, the kit may comprise particles having an antibody attached covalently or noncovalently thereto, wherein the antibody binds to C3a, to C3d, to a neoepitope of iC3b, to etc.

Any of the kits may further comprise at least one item selected from the group consisting of: instructions for use of the kit to assess complement activation; one or more native complement components or cleavage products; human serum complement, optionally characterized for levels of one or more complement components or cleavage products; serum depleted of one or more complement components or cleavage products; a detectably labeled secondary antibody; an enzyme substrate; a buffer; a diluent; a protease inhibitor; a complement inhibitor; and a support. In some embodiments the kit comprises one or more proteins or polypeptides selected from the group consisting of: C3 protein; C3d polypeptide; C3a polypeptide, iC3b polypeptide, C3b polypeptide. The kit may further comprise one or more specific binding agents that bind to any native complement component or cleavage product.

Items in a kit will often be individually wrapped or packaged in individual receptacles, which are provided together in a larger container, e.g., a cardboard or styrofoam box. Often, the reagents in the kit will have been tested and determined to be suitable for use together in an inventive method. In some embodiments reagents in the kit are suitable for use in a clinical setting, e.g., to help guide diagnosis and/or treatment of patients, as well as for research purposes. Such reagents or kits may meet specified manufacturing and/or quality control criteria. In some embodiment at least least some of the items may be manufactured according to good manufacturing practices.

The invention further provides assay systems comprising a device useful for detecting a signal, e.g., a fluorescent or luminescent or colorimetric signal, produced at least in part by a detection agent. For example the device could comprise a spectrometer, densitometer, or the like. The assay system comprises an article, e.g., a microwell plate, comprising reagents useful for performing an inventive assay. In some embodiments the assay system comprises a plate reader. In some embodiments an assay system comprises apparatus useful for performing an inventive assay in an automated and/or high throughput manner, e.g., means for automating one or more steps of the assay that might otherwise be performed manually. Apparatus robots, liquid dispensers or other liquid handling apparatus, automatic washing systems, means for moving samples or receptacles from one position to another, etc. In some embodiments, an assay system comprises a device, e.g., a computer processor, for processing data acquired by the signal detecting device, and, optionally, appropriate software for performing one or more processing steps on the data. For example such processing steps could include mathematical or statistical operations such as subtracting background, obtaining an average value or a standard deviation, obtaining a ratio, comparing values (e.g., comparing a result obtained from a sample to a normal or reference value). In some embodiments an assay system comprises means for storing data and/or results from performing an inventive assay, means for displaying or printing or otherwise outputting such data and/or results, e.g., numerically or graphically. In some embodiments an assay system comprises means for electronically transmitting data or results of an inventive assay to another device, which may or may not be physically connected with apparatus used to perform the assay or process the data. The device may be located in a different room, building, city, county, state, or country. The data or results may be transmitted wirelessly. In some embodiments the data or results are transmitted over a network, e.g., the Internet. In some embodiments the invention provides a method comprising receiving a sample, e.g., from a requestor; performing an inventive assay on the sample; and providing data or results of the assay (optionally electronically), e.g., to the requestor or the requestor's designee. The requestor can be, e.g., a researcher or a health care provider or a person or entity that acts on behalf of, or employs, such individual. In some embodiments the invention provides a method comprising furnishing a sample to a service provider; and electronically receiving data or results of an inventive assay performed on the sample. The service provider can be any person or entity capable of performing an assay. In some embodiments the method further comprises requesting the service provider (optionally electronically) to measure complement activation in the sample. In some embodiments the method further comprises obtaining the sample from a subject.

In some embodiments the invention provides a method comprising performing an inventive assay using an assay system described herein or a component thereof.

IV. Applications

The inventive methods and kits may be used in a number of applications. For example, in certain embodiments an assay of this invention may be used to assess the level of intact C3 or iC3b in a subject and/or to assess the extent to which an agent, e.g., a complement inhibitor, or a material that has the potential to activate complement, affects the level of intact C3 or iC3b in vivo or in vitro. In some embodiments, an assay of this invention may be used to assess the extent to which complement is activated and/or to assess the extent to which an agent affects, e.g. increases or decreases, complement activation in vivo or in vitro. In some embodiments, an inventive method is performed on a biological sample obtained from a subject. In some embodiments, no more than 0.1%, 0.5%, 1%, or 5% of the proteins in the sample by dry weight are complement components. In some embodiments, intact C3 or iC3b and/or complement activation are measured using an assay composition that comprises at least some substantially purified complement components. For example, a sample may contain one or more proteins, wherein at least 50% of the proteins by dry weight are complement components. In some embodiments an assay composition contains C3 and all intact complement components that lie "upstream" of C3 in one or more complement activation pathways. The assay composition may further comprise an agent that activates complement. For example, the assay composition may comprise IgM to activate the classical pathway, lipopolysaccharide to activate the alternative pathway, mannan (to activate the mannose-binding lectin portion of the lectin pathway). The ability of an agent to inhibit such activation may be assessed using an inventive assay. One may select appropriate assay conditions (e.g., temperature, pH, etc.) if it is desired to selectively activate and/or assess one of the pathways. Optionally the level of intact C3, iC3b and/or the extent of complement activation is compared with a suitable reference value. The reference value may be, e.g., a value measured from a sample that lacks one or more complement components, a value measured from a sample that lacks an agent that activates complement, a value measured from a sample obtained from a healthy individual, etc. In some embodiments an inventive assay is used to assess the effect of an agent or condition on the synthesis or secretion of C3. The assay could be used to measure intact C3 produced by, e.g., cultured hepatocytes, retinal pigment epithelial (RPE) cells, or any other cells that may synthesize C3. In some embodiments an inventive assay is used to screen for agents that inhibit or enhance synthesis and/or secretion of C3 by cells, e.g., hepatocytes or RPE cells. Such agents would be of use to modulate the complement system, e.g., for therapeutic purposes. In certain aspects, a method of the invention is of use for assessing proteolytic activity towards a complement component, e.g., proteolytic activity associated with a complement activating substance or condition.

In some embodiments, intact C3, iC3b, total C3, and/or complement activation is assessed in a blood, plasma, or serum sample obtained from a subject. In other embodiments, an inventive assay is used to assess the level of C3, iC3b, total C3, and/or complement activation in a sample of aqueous humor or vitreous humor. In some embodiments, intact C3, iC3b, total C3, and/or complement activation levels in the respiratory tract can be measured in a sputum sample. In some embodiments, intact C3, iC3b, total C3, and/or complement activation levels in a joint space can be measured in a sample of synovial fluid. In some embodiments, intact C3, iC3b, total C3, and/or complement activation levels in the CNS can be measured in a sample of CSF.

In some embodiments, an inventive assay is used to assess the effect on complement activation in vivo of an agent that has been administered to a subject. The agent is administered to the subject, and a sample is subsequently obtained. The extent of complement activation in the sample is assessed. Optionally the extent of complement activation is compared with a suitable reference value. The reference value may be, e.g., a value measured from a sample obtained from the subject prior to administration of the agent, an average value measured from samples obtained from a group of "healthy" individuals, a value that represents a desired extent of complement activation, etc. In some embodiments the agent whose effect on complement activation is assessed is a complement inhibitor. The complement inhibitor may be, e.g., a compound that inhibits at least one complement activation pathway as assessed using, e.g., any of the standard assays for complement activation described herein or known in the art. In some embodiments a complement inhibitor acts on a complement component or cleavage product, e.g., selected from C1, C3, C3b, factor B, or factor D. In some embodiments a complement inhibitor acts at or above the level of C3 convertase in a complement activation pathway, e.g., the complement inhibitor does not directly act on C5, C5 convertase, or a molecule that participates in one or more steps of complement activation that occurs in a complement activation pathway subsequent to formation of C5 convertase. In some embodiments, an inventive assay is used to assess the effect of a complement inhibitor on levels of intact C3. In some embodiments, an inventive assay is used to assess the effect of a complement inhibitor on levels of iC3b. For example, a first sample is obtained from a subject before administration of a complement inhibitor and a second sample is obtained after administration of the complement inhibitor. Optionally the subject is exposed to a complement activating stimulus prior to obtaining the second sample. In some embodiments, levels of intact C3 are measured in the samples. If the level of intact C3 in the second sample is greater than a control value (e.g., the value that would be expected had the complement inhibitor not been administered), it can be concluded that the complement inhibitor inhibited complement activation and thus inhibited consumption of intact C3. In some embodiments, levels of iC3b are measured in the samples. If the level of iC3b in the second sample is lower than a control value (e.g., the value that would be expected had the complement inhibitor not been administered), it can be concluded that the complement inhibitor inhibited complement activation and thus inhibited generation of iC3b.

Examples of agents that can inhibit one or more complement activation pathways include: antibodies that specifically bind to a complement component such as C1 (or a subunit thereof), C3, C5 (e.g., a humanized monoclonal anti-05 antibody such as 5G1.1-scFv, Pexelizumab, Eculizumab), factor B (e.g., TA106 a monoclonal antibody fragment against Factor B, or humanized versions thereof), or factor D (e.g., TNX-234, a humanized monoclonal antibody that binds Factor D); soluble complement receptors or molecules comprising them (e.g., soluble complement receptor 1 (sCR1) also known as TP10); C1-INH; certain small molecules; certain peptides, certain polypeptides comprising at least a portion of a mammalian, e.g., human, complement regulatory protein such as CFH, $CF_1$, CR1, decay accelerating factor (DAF; CD55), membrane cofactor protein (MCP; CD46), CD59, C4 bp, or CRIT (e.g., the polypeptide known as MLN2222—a fusion protein derived from DAF and MCP (U.S. Pat. No. 5,679,546); viral complement control proteins and viral complement interfering proteins (see, e.g., U.S. Ser. No. 11/612,751); naturally occurring complement inhibitors produced by bacteria, parasites, insects; and aptamers that bind to a complement component, etc. In some embodiments the complement inhibitor is compstatin or an analog thereof. Exemplary compstatin analogs are disclosed in, e.g., WO2004/026328, U.S. Ser. No. 11/605,182; and/or U.S. Ser. No. 11/544,389. In some embodiments the compstatin analog comprises a compound having a sequence set forth in Table 1 (e.g., SEQ ID NO: 28, SEQ ID NO: 32, SEQ ID NO: 34), e.g., cyclized via a bond between the cysteine residues, e.g., a disulfide bond. See Ricklin, D., et al. "Complement-targeted Therapeutics", Nature Biotechnology, 25(11):1265-75, 2007, for discussion of complement inhibitors that are or have been in preclinical or clinical development for various disorders.

TABLE 1

| Peptide | Sequence | SEQ ID NO: | Activity over compstatin |
|---|---|---|---|
| Compstatin | H-ICVVQDWGHHRCT-CONH2 | 8 | * |
| Ac-compstatin | Ac-ICVVQDWGHHRCT-CONH2 | 9 | 3 × more |
| Ac-V4Y/H9A | Ac-ICVYQDWGAHRCT-CONH2 | 10 | 14 × more |
| Ac-V4W/H9A —OH | Ac-ICVWQDWGAHRCT-COOH | 11 | 27 × more |
| Ac-V4W/H9A | Ac-ICVWQDWGAHRCT-CONH2 | 12 | 45 × more |
| Ac-V4W/H9A/T13dT —OH | Ac-ICVWQDWGAHRCdT-COOH | 13 | 55 × more |
| Ac-V4(2-Nal)/H9A | Ac-ICV**(2-Nal)QDWGA**HRCT-CONH2 | 14 | 99 × more |
| Ac V4(2-Nal)/H9A —OH | Ac-ICV**(2-Nal)QDWGA**HRCT-COOH | 15 | 38 × more |
| Ac V4(1-Nal)/H9A —OH | Ac-ICV**(1-Nal)QDWGA**HRCT-COOH | 16 | 30 × more |

TABLE 1-continued

| Peptide | Sequence | SEQ ID NO: | Activity over compstatin |
|---|---|---|---|
| Ac-V42Ig1/H9A | Ac-ICV(2-Ig1)QDWGAHRCT-CONH2 | 17 | 39 × more |
| Ac-V42Ig1/H9A —OH | Ac-ICV(2-Ig1)QDWGAHRCT-COOH | 18 | 37 × more |
| Ac-V4Dht/H9A —OH | Ac-ICVDhtQDWGAHRCT-COOH | 19 | 5 × more |
| Ac-V4(Bpa)/H9A —OH | Ac-ICV(Bpa)QDWGAHRCT-COOH | 20 | 49 × more |
| Ac-V4(Bpa)/H9A | Ac-ICV(Bpa)QDWGAHRCT-CONH2 | 21 | 86 × more |
| Ac-V4(Bta)/H9A —OH | Ac-ICV(Bta)QDWGAHRCT-COOH | 22 | 65 × more |
| Ac-V4(Bta)/H9A | Ac-ICV(Bta)QDWGAHRCT-CONH2 | 23 | 64 × more |
| Ac-V4W/H9(2-Abu) | Ac-ICVWQDWG(2-Abu)HRCT-CONH2 | 24 | 64 × more |
| +G/V4W/H9A +AN —OH | H-GICVWQDWGAHRCTAN-COOH | 25 | 38 × more |
| Ac-V4(5fW)/H9A | Ac-ICV(5fW)QDWGAHRCT-CONH$_2$ | 26 | 31 × more |
| Ac-V4(5-MeW)/H9A | Ac-ICV(5-methyl-W)QDWGAHRCT-CONH$_2$ | 27 | 67 × more |
| Ac-V4(1MeW)/W7(5fW)/H9A | Ac-ICV(1-methyl-W)QD(5fW)GAHRCT-CONH$_2$ | 28 | 264 × more |
| Ac-V4W/W7(5fW)/H9A | Ac-ICVWQD(5fW)GAHRCT-CONH$_2$ | 29 | 121 × more |
| Ac-V4(5fW)/W7(5fW)/H9A | Ac-ICV(5fW)QD(5fW)GAHRCT-CONH$_2$ | 30 | 161 × more |
| Ac-V4(5-MeW)/W7(5fW)H9A | Ac-ICV(5-methyl-W)QD(5fW)GAHRCT-CONH$_2$ | 31 | NA |
| Ac-V4(1-MeW)/H9A | Ac-ICV(1-methyl-W)QDWGAHRCT-CONH$_2$ | 32 | 264 × more |
| +G/V4(6fW)/W7(6fW)H9A +N —OH | H-GICV(6fW)QD(6fW)GAHRCTN-COOH | 33 | 126 × more |
| Ac-V4(1-formyl-W)/H9A | Ac-ICV(1-formyl-W)QDWGAHRCT-CONH$_2$ | 34 | 264 × more |
| Ac-V4(5-methoxy-W)/H9A | Ac-ICV(1-methyoxy-W)QDWGAHRCT-CONH$_2$ | 35 | 76 × more |
| G/V4(5f-W)/W7(5fW)/H9A +N —OH | H-GICV(5fW)QD(5fW)GAHRCTN-COOH | 36 | 112 × more |

N/A = not available

In some embodiments an inventive assay is used to assess a complement inhibitor or a complement activator in vitro. The complement activator can be any substance that activates complement as assessed using, e.g., any of the standard assays for complement activation described herein or known in the art. Examples of agents known to activate complement are: bacterial cell wall components such as LPS or carbohydrates, antigen-antibody complexes, etc. In some embodiments the agent is an agent being tested to determine its effect on complement activation. In some embodiments the agent is a therapeutic agent whose mechanism of action is at least in part mediated by complement. The agent may be an antibody that activates complement on target cells such as cancer cells, immune system cells that play a role in autoimmune disease, or pathogens. Examples of such agents include antibodies that bind to various cell surface molecules such as CD20, EGFR, HER2, or other growth factor receptors. Specific examples include rituximab, cetuximab, trastuzumab, and alemtuzumab. In some embodiments, measurements are made on samples obtained at multiple time points, optionally starting before administration of an agent, thereby providing an indication of the extent to which the agent modulates complement activation and the time course and duration of the modulation.

In some embodiments of the invention, information obtained from an inventive assay is used to provide prognostic, diagnostic, or therapeutic information relating to a subject. "Prognostic information" can include information regarding the likelihood that a subject will develop a disease or condition and/or information regarding the possible outcome, time course, or progression of a disease or condition (e.g., with or without therapy), etc. "Diagnostic information" can include information regarding the likelihood that a subject has a disease or condition and/or information about the particular features of such disease or condition as manifested in the subject. "Therapeutic information" can include information regarding a suitable treatment or therapeutic regimen for the subject. For example, therapeutic information can include whether to administer a therapeutic agent, which agent or class of agents is appropriate, which dose and dosing schedule to select, whether and when to retreat, whether to cease therapy, etc. In some embodiments, e.g., embodiments in which the therapeutic agent is a complement inhibitor, the disorder is a complement-mediated disorder, i.e., one in whose development, progression, or manifestation(s) complement activation plays a role. In some embodiments the condition is associated with complement deficiency.

In some embodiments the level of intact C3, iC3b, total C3, or complement activation in a sample comprising, e.g., serum, plasma, or blood from a subject are determined, and the result is used to provide prognostic, diagnostic, or therapeutic information. For example, results of an inventive assay may be used, optionally together with information regarding the subject's genotype with respect to one or more alleles or polymorphisms that have been associated with increased or decreased risk of developing a disease and/or with increased or decreased risk of progression of a disease, in order to provide prognostic, diagnostic, or therapeutic information. In some embodiments, the genotype is obtained with respect to particular alleles of one or more complement components or complement regulatory proteins. For example, in some embodiments the genotype is determined with respect to a polymorphic site in a gene that encodes a protein selected from the group consisting of: complement factor H(CFH), complement proteins C2, C3, factor B, C7, complement factor I, a CFH-like protein (e.g., CFHR1, CFHR1, CFHR3, CFHR4, and CFHR5), and MBL-2.

In some embodiments, the disorder is an ocular disorder (e.g., a disease that only or primarily affects the eye). Exemplary ocular disorders are macular degeneration, e.g., age-related macular degeneration (AMD), diabetic retinopathy, glaucoma, and uveitis. AMD is an ocular disorder that is characterized by degenerative changes in the macula, the area of the retina that provides high visual acuity and contains a dense concentration of cones, the photoreceptors that are responsible for color vision. AMD causes a progressive loss in central vision and is the most common cause of functional blindness in developed countries for those over 50 years of age. AMD has been classified into dry (non-exudative) and wet (exudative) forms. The wet form, which affects about 10-15% of those with AMD, is characterized by progressive growth of new blood vessels (neovascularization) in the back of the eye. Pathologic neovascularization can cause rapid deterioration in vision as a consequence of fluid leakage and, in the longer term, retinal fibrosis and scarring. The majority of individuals with AMD suffer from the dry form of the disorder, which is characterized by atrophy and dysfunction or retinal tissues but lacks the ocular neovascularization present in the wet form. Dry AMD can cause serious vision loss, and persons with dry AMD are at increased risk of progressing to the wet form. In the Age-Related Eye Disease Study (AREDS), individuals were classified into AREDS category 1 (No AMD—no or few small drusen <63 microns in diameter), AREDS category 2 (consisting of a combination multiple small drusen (<63 microns in diameter), few intermediate drusen (63-124 microns in diameter), or RPE abnormalities), AREDS category 3 (consisting of extensive intermediate drusen, at least one large drusen (≥125 microns in diameter)), or GA not involving the center of the fovea), or AREDS 4 (GA involving the center of the fovea or exudative AMD). Further information regarding AMD is found in the following: Jager, R., et al., N. Engl. J. Med.:358:2606-17, 2008, and other references cited herein. See also, American Academy of Ophthalmology Retina Panel. Preferred Practice Pattern® Guidelines. Age-Related Macular Degeneration. San Francisco, Calif.: American Academy of Ophthalmology; 2008, available at www.aao.org./ppp.

A variety of clinical and imaging modalities may be used to assess subjects at risk of or suffering from AMD. Visual acuity can be measured using, for example, a Snellen chart, a Bailey-Lovie chart, a decimal progression chart, a Freiburg visual acuity test, a measurement of minimum angle of resolution (MAR) etc. Metamorphopsia (visual distortion) may be measured using an Amsler chart. Contrast sensitivity may be measured using a Pelli-Robson chart. Diagnostic studies include, but are not limited to, standard ophthalmologic examination of the fundus, stereo biomicroscopic examination of the macula, intravenous fundus fluorescein angiography, fundus photography, indocyanine green video-angiography, optical coherence tomography, autofluorescence studies, and other imaging techniques. An individual who would be recognized as having AMD by one of skill in the art based on appropriate physical findings, imaging tests, and/or other appropriate criteria is considered to have "clinically evident AMD".

The present invention provides, in some aspects, new approaches for assessing subjects at risk or or suffering from AMD. Surprisingly, it was found that individuals that had been diagnosed with AMD had significantly higher serum levels of intact C3 than control individuals over 60 years of age not diagnosed with AMD (see Example 9). Notably, the levels of intact C3 found in the two groups of samples (from individuals with or without diagnosed AMD) fell into two non-overlapping ranges, with the exception of one sample in the control (non-AMD) group (which might have represented an undiagnosed case of AMD or a subject developing but not yet having clinically evident AMD). The invention encompasses the recognition that levels of intact C3 (e.g., blood, serum, or plasma levels) can be used as a biomarker for AMD. The invention provides methods of using the level of intact C3 in a biological sample, e.g., blood, serum, or plasma, to provide prognostic, diagnostic, or therapeutic information relating to AMD. In some embodiments of the invention, the level of intact C3 is used to assess whether a subject has or is at increased risk of developing clinically evident AMD. By "at increased risk of developing clinically evident AMD" is meant that the subject has a greater likelihood of developing clinically evident AMD than the average likelihood that an individual of the same age but not having an increased level of intact C3 has of developing clinically evident AMD. In some embodiments the subject is at increased risk of developing clinically evident AMD within the subsequent 6 months, 1 year, 2 years, or 5 years. The subject may be in the process of developing AMD, i.e., their condition is progressing towards clinically evident AMD.

The invention provides a method for assessing whether a subject has, or is at increased risk of developing, age-related macular degeneration (AMD), or is at increased risk of progressing from early AMD to more advanced AMD, comprising detecting intact C3 in a sample comprising serum, plasma, or whole blood from the subject, wherein a level of intact C3 that is greater than a control level indicates that the individual has or is at increased risk of developing AMD, or is at increased risk of progressing from early AMD to more advanced AMD. In some embodiments the control level is an average level found in a control population composed of individuals not having AMD. In some embodiments the control population is composed of individuals at least 60 years of age not having AMD. In some embodiments the control population is composed of individuals not having AMD who are within 5 years, or within 10 years, of the age of the subject.

The invention also provides a related method for assessing whether a subject has, or is at increased risk of developing, age-related macular degeneration (AMD), or is at increased risk of progressing from early AMD to more advanced AMD, comprising detecting intact C3 in a sample comprising serum, plasma, or whole blood from the subject, wherein a level of intact C3 that is within a range associated with increased likelihood of having or developing AMD or associated with increased risk of progressing from early AMD to more advanced AMD, indicates that the individual has or is at increased risk of developing AMD, or is at increased risk of progressing from early AMD to more advanced AMD.

In some embodiments the method of assessing the level of intact C3 comprises detecting intact C3 using an ELISA assay. In some embodiments the method comprises capturing intact C3 using a monoclonal antibody that binds to C3a and detecting captured intact C3 using a polyclonal antibody that binds to C3. In some embodiments the method comprises capturing intact C3 using a monoclonal antibody that binds to C3a and detecting intact C3 using a polyclonal antibody that binds to C3d and does not significantly recognize C3 epitopes outside C3d. In some embodiments the monoclonal antibody is mouse anti-human C3a/C3 antibody #HM2075 (Cell Sciences) or an antibody that binds to the same epitope.

In some embodiments the subject has not been diagnosed with AMD, and an increased level of intact C3 relative to a control level indicates that the subject is developing AMD, e.g., the subject is progressing towards clinically evident AMD. In some embodiments the subject has not been diagnosed with AMD, and an increased level of intact C3 indicates that the subject is at increased risk of manifesting clinically evident AMD, e.g., within the following 6 months, 1 year, 2 years, 5 years, or 10 years, relative to the likelihood that a subject not having an increased level of intact C3 would have.

In some embodiments, the individual has early AMD, and a level of intact C3 that is greater than a control level indicates that the individual is at increased risk of progressing from early AMD to more advanced AMD, e.g., within the following 6 months, 1 year, 2 years, 5 years, or 10 years, relative to the likelihood that a subject not having an increased level of intact C3 would have of progressing. In some embodiments, the individual has early AMD, and a level of intact C3 that is greater than a control level indicates that the individual is progressing to more advanced AMD. In some embodiments of the invention, the level of intact C3 is used to assess whether a subject with early AMD (e.g., AREDS 2) is at increased risk of progressing to more advanced AMD such as AMD with geographic atrophy or wet AMD, i.e., to assess whether a subject with early AMD has a greater likelihood of developing more advanced AMD than the average likelihood that an individual with early AMD has of developing advanced AMD. In some embodiments of the invention, the level of intact C3 is used to assess whether a subject with GA not involving the fovea is at increased risk of progressing to GA involving the fovea, i.e., to assess whether a subject with GA not involving has a greater likelihood of progressing to GA involving the fovea than the average likelihood that an individual with GA not involving the fovea has of progressing to GA involving the fovea. In some embodiments, the increased level is greater than the control level by a statistically significant amount. In some embodiments, the increased level is at least 1.5 times the average control level. In some embodiments, the increased level is at least 2 times the average control level. In some embodiments the likelihood is increased by a factor of at least 1.2, at least 1.5, at least 2, at least 2.5, at least 3, at least 4, at least 5, or more.

In some embodiments, intact C3 levels are monitored at various times (e.g., annually), e.g., in individuals over age 50. If the level of intact C3 exceeds a predetermined value and/or exhibits a significant increase as compared with a previously determined level, the individual is started on appropriate therapy, e.g., with a potent compstatin analog. In some embodiments, intact C3 levels are monitored over time in individuals with early AMD. If the level of intact C3 exceeds a predetermined value and/or exhibits a significant increase as compared with a previously determined level, the individual is started on appropriate therapy, e.g., with a potent compstatin analog.

The invention also provides a method for assessing whether a subject has or is at increased risk of developing age-related macular degeneration (AMD) comprising determining the level of one or more proteins in a sample comprising serum, plasma, or whole blood from the subject using a monoclonal antibody that binds to C3a/C3, wherein a level of said one or more proteins that is greater than a control level indicates that the individual has or is at increased risk of developing AMD. In some embodiments, the protein(s) is/are detected using an ELISA assay. In some embodiments the method comprises capturing protein(s) using a monoclonal antibody that binds to C3a/C3 and detecting captured intact C3 using a polyclonal antibody that binds to C3. In some embodiments the method comprises capturing protein(s) using a monoclonal antibody that binds to C3a/C3 and detecting intact C3 using a polyclonal antibody that binds to C3d and does not significantly recognize C3 epitopes outside C3d. In some embodiments the monoclonal antibody is mouse anti-human C3a/C3 antibody #HM2075 (Cell Sciences) or an antibody that binds to the same epitope.

In some embodiments the subject has not been diagnosed with AMD, and an increased level of proteins captured using the antibody relative to a control level indicates that the subject is developing AMD, e.g., the subject is progressing towards clinically evident AMD. In some embodiments the subject has not been diagnosed with AMD, and an increased level of proteins captured using the antibody indicates that the subject is at increased risk of manifesting clinically evident AMD, e.g., within the following 6 months, 1 year, 2 years, 5 years, or 10 years, relative to the likelihood that a subject not having an increased level of intact C3 would have.

In some embodiments, the individual has early AMD, and a level of proteins captured using the antibody that is greater than a control level indicates that the individual is at increased risk of progressing from early AMD to more advanced AMD, e.g., within the following 6 months, 1 year, 2 years, 5 years, or 10 years, relative to the likelihood that a subject not having an increased level of proteins captured using the antibody would have of progressing. In some embodiments, the individual has early AMD, and a level of proteins captured using the antibody that is greater than a control level indicates that the individual is progressing to more advanced AMD. In some embodiments of the invention, the level of proteins captured using the antibody is used to assess whether a subject with early AMD (e.g., AREDS 2) is at increased risk of progressing to more advanced AMD such as AMD with geographic atrophy or wet AMD, i.e., to assess whether a subject with early AMD has a greater likelihood of developing more advanced AMD than the average likelihood that an individual with early AMD has of developing advanced AMD. In some embodiments of the invention, the level of proteins captured using the antibody is used to assess whether a subject with GA not involving the fovea is at increased risk of progressing to GA involving the fovea, i.e., to assess whether a subject with GA not involving has a greater likelihood of progressing to GA involving the fovea than the average likelihood that an individual with GA not involving the fovea has of progressing to GA involving the fovea. In some embodiments, the increased level is greater than the control level by a statistically significant amount. In some embodiments, the increased level is at least 1.5 times the average control level. In some embodiments, the increased level is at least 2 times the average control level. In some embodiments the likelihood is increased by a factor of at least 1.2, at least 1.5, at least 2, at least 2.5, at least 3, at least 4, at least 5, or more.

In some embodiments, the level of proteins captured using the antibody is monitored at various times (e.g., annually), e.g., in individuals over age 50. If the level exceeds a predetermined value and/or exhibits a significant increase as compared with a previously determined level, the individual is started on appropriate therapy, e.g., with a potent compstatin analog. In some embodiments, levels are monitored over time in individuals with early AMD. If the level exceeds a predetermined value and/or exhibits a significant increase as compared with a previously determined level, the individual is started on appropriate therapy, e.g., with a potent compstatin analog.

Results of an inventive assay may be used, optionally in conjunction with one or more other assays and/or information obtained from one or more clinical or laboratory evaluations. to provide prognostic, diagnostic, or therapeutic information. For example, results of an inventive assay, optionally together with information obtained from an ophthalmoscopic examination, other physical examination, genetic evaluation, risk factor evaluation (e.g., diet, smoking status, age), family history, etc., can be used to provide prognostic, diagnostic, or therapeutic information. In some embodiments, results of an inventive assay may be used, optionally together with information regarding the subject's genotype with respect to one or more alleles or polymorphisms that have been associated with increased or decreased risk of developing a disease and/ or with increased or decreased risk of progression of a disease. In some embodiments, the genotype is obtained with respect to particular alleles of one or more complement components or complement regulatory proteins. For example, in some embodiments the genotype is determined with respect to a polymorphic site in a gene that encodes a protein selected from the group consisting of: complement factor H(CFH), complement proteins C2, C3, factor B, C7, complement factor I, a CFH-like protein (e.g., CFHR1, CFHR1, CFHR3, CFHR4, and CFHR5), and MBL-2.

Genetic studies have identified strong associations between alleles of a number of complement components and complement regulatory proteins and the risk of developing AMD. See, e.g., Li, M, et al., Nat Genet, 38:1049-54, 2006 (see, Tables 1 and 2); Gold, B., et al., Nat. Genet, 38: 458-62, 2006; Dinu, V., et al., Genetic Epidemiology, 31: 224-237, 2007 (see, e.g., Tables 3 and 5), Yates, J. R. W., N. Engl. J. Med., 357: 19-27, 2007 (see, e.g., Tables 2 and 3), Francis, P., et al., PLoS ONE. November 28; 2(11):e1197, 2007 (see, e.g., Tables 1 and 2 therein), Fagerness J A, et al., Eur J Hum Genet., 17(1):100-4, 2009; Bergeron-Sawitzke J, et al., Eur J Hum Genet. 2009 Mar. 4. [Epub ahead of print]. Polymorphisms linked to altered AMD susceptibility include rs1061170, rs1047286, rs2230199, rs120862610, rs9332739, rs547154, rs4151667, rs641153, rs41015361, rs33682798, rs10490924, and rs1045216. Polymorphic sites in age-related maculopathy susceptibility (ARMS2) and/or HtrA serine peptidase 1 (HTRA1) loci are also associated with altered, e.g., increased, susceptibility to AMD. In some embodiments, results of an inventive assay are used, optionally together with genotype information with respect to one or more alleles that are associated with increased or decreased risk of developing AMD, to provide prognostic, diagnostic, or therapeutic information. In some embodiments, an increased level of complement activation as assessed using an inventive assay, together with presence of one or more risk alleles for AMD indicates that the subject has an increased likelihood of developing AMD or of progressing rapidly from an early form of dry AMD (e.g., AREDS 2) to a more advanced form such as geographic atrophy (GA) or of progressing from dry AMD to wet AMD or of a subject with wet AMD developing GA, relative to the likelihood that a subject having the risk allele but not having an increased level of intact C3. In some embodiments, an increased level of intact C3, together with presence of one or more risk alleles for AMD indicates that the subject has an increased likelihood of developing AMD or of progressing rapidly from an early form of dry AMD (e.g., AREDS 2) to a more advanced form such as geographic atrophy (GA), relative to the likelihood that a subject having the risk allele but not having an increased level of intact C3. In some embodiments the methods allow one to identify subjects who are likely to progress to clinically evident AMD within a subsequent time period such as the 6 months, 1 year, or 2 years after the assay was performed. In some embodiments the methods allow one to identify subjects who are not likely to progress to clinically evident AMD within a subsequent time period such as the 6 months, 1 year, or 2 years after the assay was performed. Based at least in part on such information, an appropriate therapy, e.g., an appropriate complement inhibitor therapy, e.g., therapy with a potent compstatin analog, may be recommended to a subject. See, e.g., U.S. Ser. No. 11/544,389 and PCT/US08/78593. See also PCT/US07/01649. Based at least in part on such information, a health care provider may select complement inhibitor therapy for a subject. The subject may, for example, have drusen whose phenotype indicates an increased likelihood that the subject will develop AMD within 5 years time (versus the likelihood that an appropriately matched subject without drusen would develop AMD within 5 years). If the subject additionally has an elevated level of intact C3, therapy is initiated. In other embodiments the subject may have early dry AMD that has not progressed to GA. If the subject additionally has an elevated level of intact C3, therapy is initiated. On the other hand, if the subject does not have an elevated level of intact C3, the subject can continue being monitored without initiating therapy. In some embodiments an assay of the invention is used, optionally together with genotype, clinical, imaging, or other data, to decide when to initiate complement inhibitor therapy. Samples (e.g., blood or anterior chamber fluid) are obtained at various time points (e.g., approximately monthly, every 6-8 weeks, etc.) from a subject at risk of AMD or of progressing from early to intermediate or from intermediate to advanced AMD, and an inventive assay is performed. In some embodiments, if the level of intact C3 in the subject's blood rises above a specified value, complement inhibitor therapy is initiated. In some embodiments, if the level of complement activation rises significantly above a specified value, complement inhibitor therapy is initiated. The specified value may be, e.g., the average value found in a population of subjects not suffering from AMD (e.g., subjects above 60 years of age), or between 1 and 5 times such value. In some embodiments, a complement inhibitor is administered to a subject suffering from AMD, e.g., early, intermediate, or advanced AMD (wet AMD or GA involving the fovea) in one or both eyes. Samples (e.g., blood or anterior chamber fluid) are obtained at various time points (e.g., approximately monthly, every 6-8 weeks, etc.) and an inventive assay performed. If the level of complement activation rises above a specified value, the subject is retreated with the complement inhibitor. The specified value may be, e.g., the average value found in a population of subjects not suffering from AMD, or a fraction of such value, e.g., a fraction between 1/20 and 1.

In some embodiments an inventive method is used to provide prognostic, diagnostic or therapeutic information, wherein the disorder is a renal disease (e.g., a disease that exclusively or primarily affects the kidney) or a systemic disease that has renal manifestations, e.g., glomeruloephritis, e.g., glomerulonephritis with C3 deposition such as membranoproliferative glomerulonephritis (MPGN) or atypical haemolytic uraemic syndrome (aHUS).

In some embodiments, an inventive method is used to provide prognostic, diagnostic or therapeutic information, wherein the disorder is one that affects the cardiovascular system, such as atherosclerosis or restenosis (e.g., following an intervention such as angioplasty, balloon dilation, laser ablation, or stent placement). In some embodiments an inventive assay is used to monitor complement activation over time in a subject who suffers from or is at risk of a disorder affecting the cardiovascular system, and a complement modulating agent is administered so as to keep the level of complement activation within desired values. For example, the subject may have suffered a myocardial infarction, may have elevated cholesterol (e.g., LDL cholesterol) and/or triglycerides, a family history of cardiovascular disease, etc. The desired value may be, e.g., the average value found in a population of subjects, e.g., a population of subjects not suffering from a cardiovascular disorder, or a fraction of such value, e.g., a fraction between 5% and 99% of such value.

In some embodiments the subject has suffered an injury, e.g., a serious physical injury such as an open wound, blunt injury, or major burns. In some embodiments of the invention the subject suffers from traumatic brain injury or spinal cord injury. In some embodiments the subject has suffered an injury sufficiently severe to warrant admission to hospital or to an intensive care unit. In some embodiments the subject has an injury severity score (ISS) of at least 9. In some embodiments the subject has an injury severity score (ISS) of at least 15. The Injury Severity Score (ISS) is an anatomical scoring system that provides an overall score for patients with multiple injuries Baker S P et al, "The Injury Severity Score: a method for describing patients with multiple injuries and evaluating emergency care", J Trauma 14:187-196, 1974. The ISS score is the most widely used anatomical scoring system for injury and correlates linearly with mortality, morbidity, hospital stay and other measures of severity. In some embodiments an inventive assay is used to monitor complement activation over time in a subject who has recently suffered severe physical injury and a complement modulating agent is administered so as to keep the level of complement activation within desired values. In some embodiments "recently" refers to within the preceding 24, 48, 72, 96, or 120 hours. In some embodiments "recently" refers to within the preceding 1, 2, 3, 4, 5, 6, 7, 10, 14, 21, or 28 days. The desired value may be, e.g., the average value found in a population of subjects not suffering from severe injury, or a fraction thereof, e.g., a fraction between 5% and 99% of such value. In some embodiments the desired value is greater than the average value found in subjects not suffering from severe injury. For example, the desired value may be between 0.5 and 5 times such value.

In some embodiments the subject has recently suffered an event associated with ischemia (e.g., an ischemic stroke or a heart attack). In some embodiments the subject is at risk of or suffers from ischemia/reperfusion injury. In some embodiments the subject has suffered a hemorrhage.

In some embodiments the subject has experienced an adverse reaction to a drug or a reaction to an environmental antigen, food, toxin, venom, etc.

In some embodiments of the invention the disorder is selected from the group consisting of alopecia greata, anklosing spondylitis, antiphospholipid syndrome, asthma, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue, chronic fatigue syndrome immune deficiency, syndrome (CFIDS), chronic inflammatory demyelinating polyneuropathy, chronic obstructive pulmonary disease (COPD), cicatricial pemphigoid, cold agglutinin disease, Crest syndrome, Crohn's disease, Dego's disease, dermatitis, dermatomyositis, discoid lupus, essential mixed cryoglobulinemia, fibromyalgia—fibromyositis, glomerulonephritis, Grave's disease, Guillain-Barre sydrome, Hashimoto's thyroiditis, idiopathic pulmonary fibrosis, idiopathic thrombocytopenia purpura (ITP), IgA nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, rheumatoid arthritis, polymyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, systemic lupus erythematosus, Takayasu arteritis, temporal arteritis/giant cell arteritis, ulcerative colitis, uveitis, vasculitis, vitiligo, and Wegener's granulomatosis.

EXAMPLES

Example 1

Identification of a Monoclonal Antibody Suitable for Capturing or Detecting Intact C3

Figure 2A:
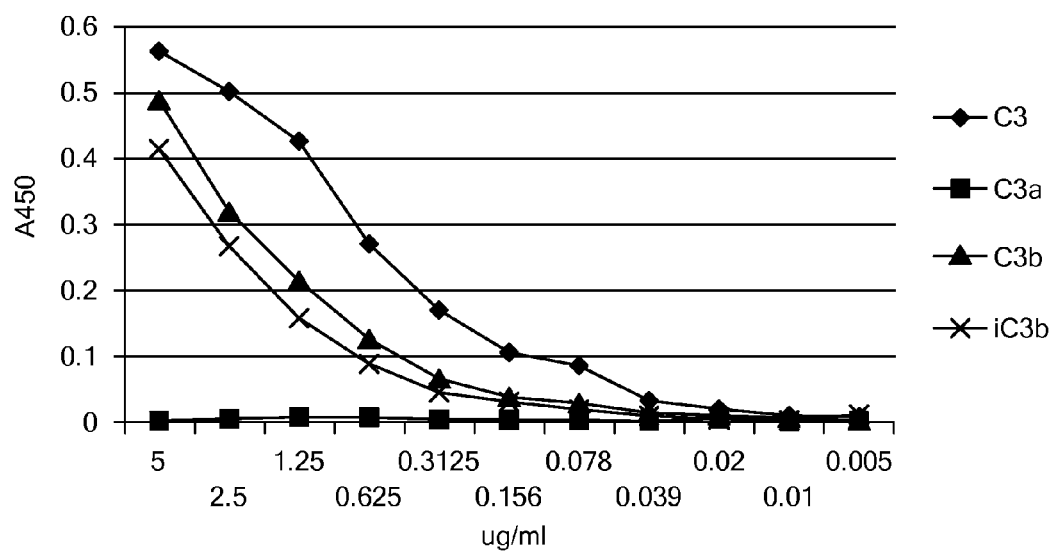
Figure 2B:
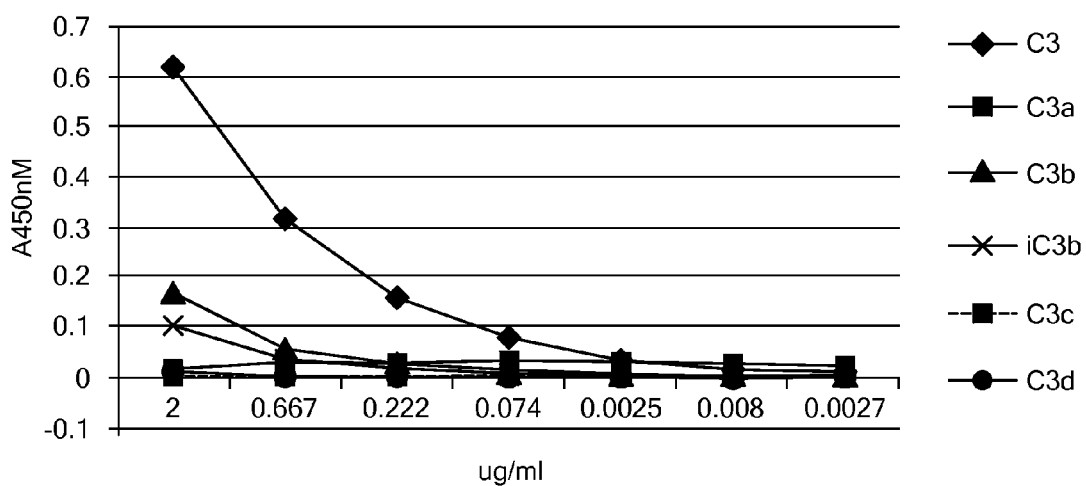
Figure 2C:
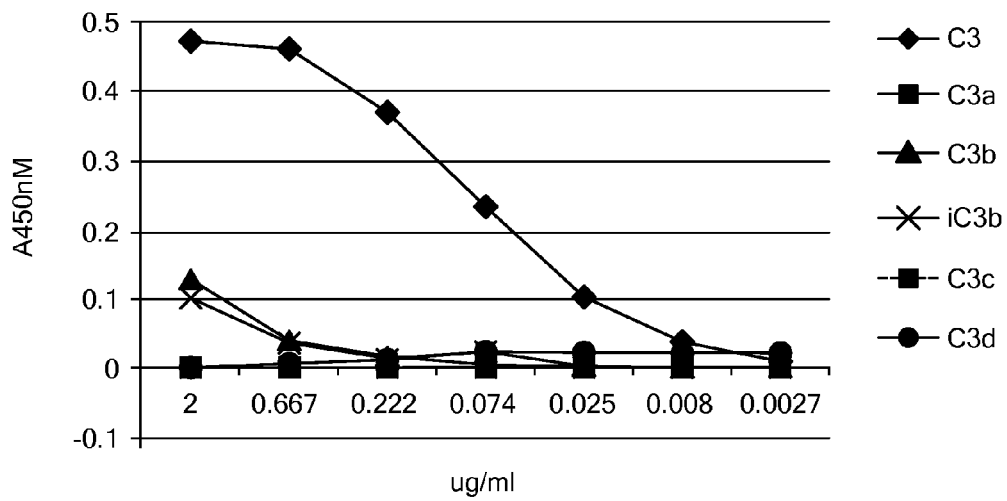
FIG. 2c shows results of an ELISA assay in which anti-human C3a mAb HM 2073 (Cell Science) was used as capture antibody. The plate was coated with 100 ng/well mouse anti-C3a. In each case, goat anti-C3-HRP was used as detection antibody.

The following seven antihuman C3a/C3 Abs were tested in ELISA assays as capture antibodies for intact C3 using goat anti-C3-HRP as a detection antibody: mouse anti-C3a (Quidel, A203; Cell Sciences HM2073, HM2074, HM2075), chicken anti-C3a (Abcam ab48580; Genetex, GTX 78198) and goat anti-C3a (SantaCruz, sc17237). The experiments were performed according to the protocol described in Example 2. Considerable variability was observed in the specificity of these antibodies. For example, as shown in FIG. 2a, the anti-C3a Ab $A_2O_3$ lacks specificity, it can bind C3b and iC3b as well. Cell Science HM 2073 and HM 2075 showed good specificity when detecting individual complement components (FIGS. 2b and 2c).

Example 2

Assay for Determining Concentration of Intact C3

This example describes a method of determining the concentration of intact C3 in human plasma or serum samples.
General:
1. Complement proteins, serum samples and antibody are kept on ice;

2. During dilution, samples are mixed by slowly pipetting up and down or inverting the tubes a few times;
3. Serum is thawed quickly in 37° C. water bath and immediately transferred to ice;
4. Caution is exercised not to let the wells dry out during the procedure;
5. Pipetting tips are changed during each serial dilution.

Procedure:
1. Plate: Thermo Scientific ultrahigh binding 96 well plate Immulon 4HBX (Thermo Scientific, 3855);
2. Coating: Monoclonal antibody mouse anti-C3/C3a, (Cell Sciences, HM2073) dilute stock to 2 ug/ml in PBS, add 50 ul per well, cover the plate with a plate sealer and incubate overnight at 2-8° C. or room temperature for 1-2;
3. Blocking: Block with Pierce blocking buffer or 1% BSA solution in PBS, add at least 200 ul to each well, incubate 1-2 h at room temperature;
4. Standard and sample preparation: Standards and samples will be diluted in blocking buffer. Serial dilution of pure human C3 protein (Complement Technology, A113) is used to generate standard curve. Wash the plate 3 times and add 50 ul of samples to each well. Incubate 1 h at room temperature.
5. Detection antibody: Wash plate 6 times before adding detection antibody. Dilute Goat anti-C3-HRP (MP Biomedicals, 55237) 1:5000 with blocking buffer and add 50 ul to each well, incubate 1 h at room temperature OR dilute chicken anti-human-C3-HRP (Immunology Consultants Laboratory) 1: 2000 dilution add 50 ul to each well, incubate 1 h at room temperature.
6. Substrate: Wash the plate 6 times, and add 50 ul/well of TMB substrate solution (BD Bioscience, 555214) incubate the plate for 5 to 10 min at room temperature in the dark. Add 25 ul/well of 1M $H_2SO_4$ to stop the reaction. Measure OD within 10 min at 450 nM.

Interpretation of Results:

Standard Curve:

A standard curve is generated for each run using healthy human serum as diluents. The optimal dilution for each complement component assay is determined by testing serum dilutions from healthy subjects and patients. A dilution that yields A450 value around 0.2-0.5 is selected. The standard curve will use the same dilution factor to dilute healthy human serum and will use it as diluent. The average serum absorbance is subtracted from complement standard absorbance value to get the net absorbance value A450. The standard curve is prepared by plotting the net absorbance values A450 of each standard on the y-axis and corresponding concentration indicated on the x-axis. A four parameter curve fit (e.g., available in Microsoft Excel) is used to generate the equation.

Calculation of Results:

The average dilution buffer absorbance is subtracted from all the sample absorbance value to get the net absorbance value. The four-parameter curve fitting equation is used to calculate the unknown sample concentration (x) from the known absorbance value (y).

Example 3

Measuring Intact C3 in Samples Containing Human Serum

Figure 3A:
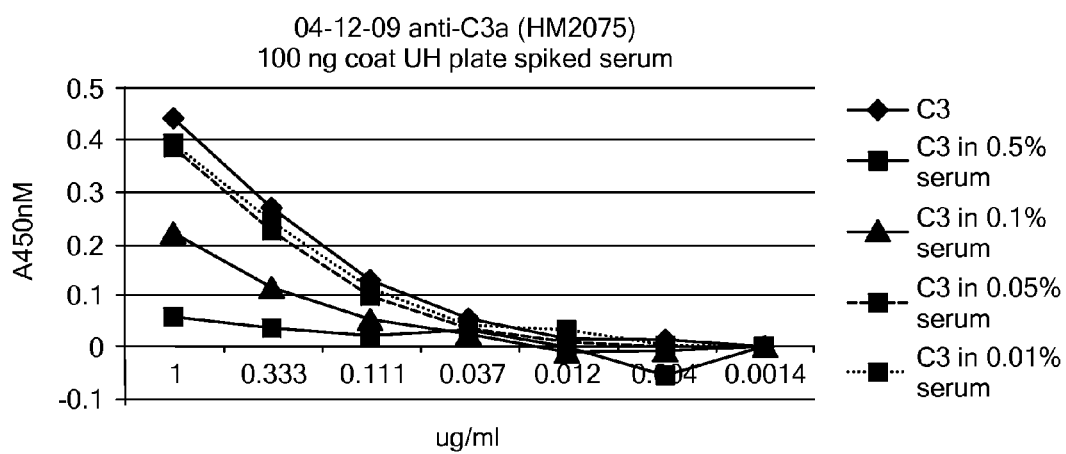
Figure 3C:
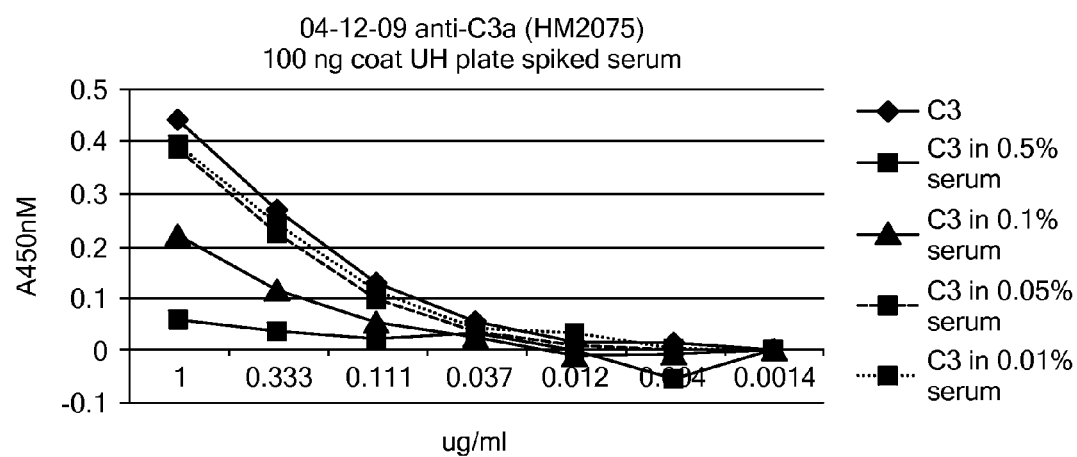

The protocol described in Example 2 was used to assess C3 levels in serum samples at different dilutions to which C3 had been added. C3 was captured using HM2073 or HM2075 anti-C3a/C3 mAb (100 ng coating per well), and detected using goat anti-C3-HRP. The data for HM2073 are plotted in FIG. 3a. The data for HM2075 are plotted in FIG. 3c. Tables 2-5 (FIGS. 3b and 3d) show the raw and processed data obtained in these experiments. Rows A-H of Tables 2 and 4 correspond to wells of a 96-well plate. The samples in the wells corresponding to row A are serially diluted 3-fold moving downwards. Data in rows A-F, columns 1-10 is from wells containing different concentrations of C3 as follows: row A: 1.0 µg/ml; row B 0.333 µg/ml: row C, 0.111 mg/ml; row D: 0.037 µg/ml; row E: 0.012 µg/ml; row F: 0.004 µg/ml. Data for the 0.001 pg/ml concentration is not shown. Data in rows G and H is from wells that contain matrix only (i.e., 0 µg/ml C3). The average values for the different matrices are shown in row I. BB stands for blocking buffer.

Each set of two columns in Tables 2 and 4 represents results from duplicate wells containing C3 at varying concentrations ranging from 1.0 µg/ml to 0 µg/ml (depending on the row) in a different matrix. The matrices are as follows: columns 1 and 2: blocking buffer; columns 3 and 4: 0.5% serum; columns 5 and 6: 0.1% serum; columns 7 and 8: 0.05% serum; columns 9 and 10: 0.01% serum; columns 11 and 12: 0.5% serum. Please note that the matrices are diluted moving downwards from row A.

The first column in Tables 3 and 5 shows the C3 concentrations corresponding to the data in each row except for the data in the rightmost column, which is obtained from wells containing serum only. For example, data in the top row corresponds to wells containing C3 at 1 µg/ml. Data in Tables 3 and 5 is obtained by averaging the two corresponding values in Tables 2 and 4 and subtracting the relevant background value associated with the matrix. For example, the value 0.0308 in the second row (labeled 0.333), fifth column (labeled C3 in 0.05% serum) of Table 3 was obtained by averaging 0.423 and 0.424 (from row B, columns 7 and 8 of Table 2) and subtracting 0.116 (from row I, column 7 of Table 2).

Example 4

Specificity of the Assay for Intact C3

The specificity of the assay for intact C3 described in Example 2 was tested using mock samples containing purified complement components either individually or in mixtures.

Figure 4A:
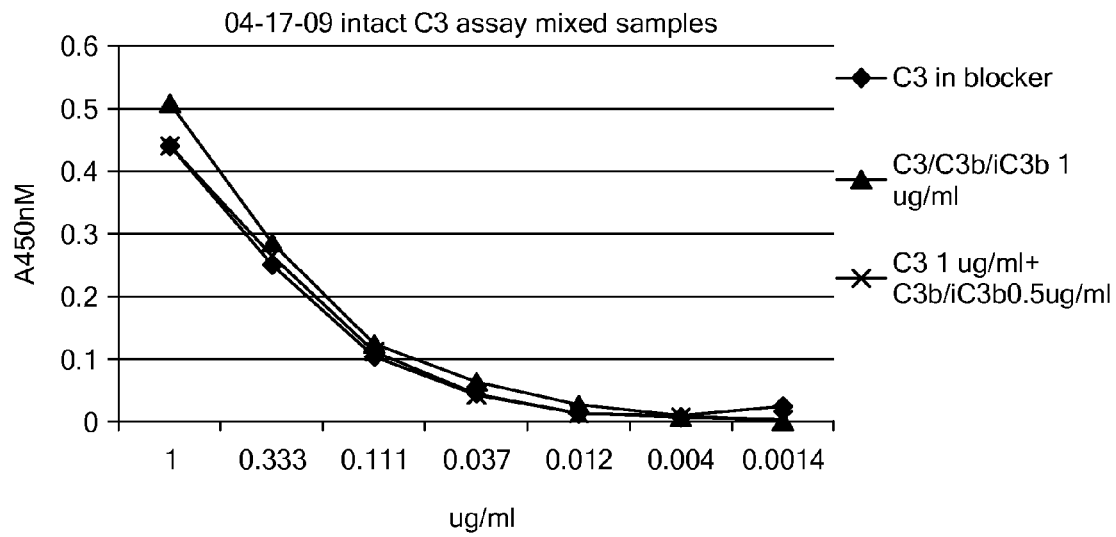
FIGS. 4a and 4b show detection of intact C3 in the presence of C3b and iC3b, showing specificity of the assay.
Figure 4B:
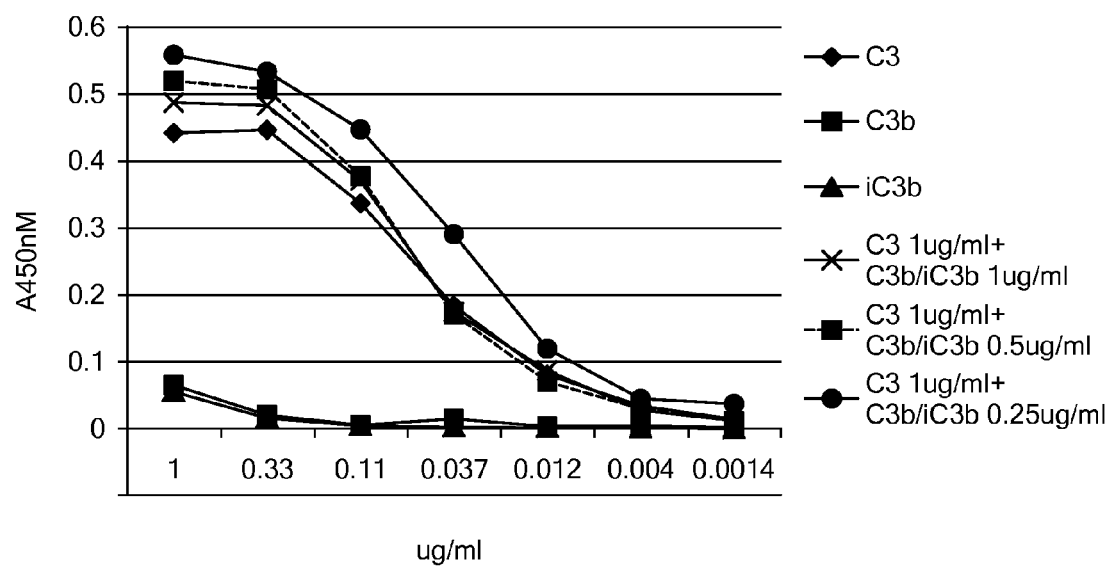

In one set of experiments 1 µg/ml each of human purified complement proteins C3, C3b and iC3b, or 1 µg/ml of C3 and 0.5 µg/ml each of C3b and iC3b were loaded into the left most well of each row of a 96-well plate. The diluent was blocking buffer. Twofold dilutions of each sample were then made moving rightward across the plate. The concentration of intact C3 in each sample was measured using the assay described in Example 2. Results of a representative assay are shown in FIG. 4a and demonstrate that there is no significant crosstalk with either iC3b or C3b. FIG. 4b shows results of experiments in which intact C3 was assayed in samples that contained 1 µg/ml of C3 and also contained both C3b and iC3b protein in amounts ranging from 0.25 µg/ml to 1 µg/ml. FIG. 4b shows that intact C3 is accurately detected in the presence of levels of other C3 products at relative ratios to C3 higher than would be expected in patient samples. For example, the readout from the sample containing 1 pg/ml each of C3, iC3b, and C3b (purple x) is almost identical to that obtained from the sample containing 1 µg/ml of C3 only (blue diamonds).

Example 5

Assay for Determining Concentration of iC3b

This example describes a method of determining the concentration of iC3b in human plasma or serum samples.
General: As described in Example 2.
Procedure:
1. Assay plate: Thermo Scientific Immnulon 1 B medium binding 96 well plate (Thermo Scientific, 3355);
2. Coating: mouse anti-iC3b (Quidel, A209), dilute stock to 2 ug/ml in PBS, add 50 ul per well, cover the plate with a plate sealer and incubate overnight at 2-8° C. or room temperature for 1-2;
3. Blocking: Block with Pierce blocking buffer or 1% BSA solution in PBS, add at least 200 ul to each well, incubate 1-2 h at room temperature;
4. Standard and sample preparation: Standards and samples will be diluted in blocking buffer. Serial dilution of pure human iC3b (Complement Technology, A 115) is used to generate standard curve. Wash the plate 3 times and add 50 ul of samples to each well. Incubate 1 h at room temperature.
5. Detection antibody: Wash plate 6 times before adding detection antibody. Dilute Goat anti-C3-HRP (MP Biomedicals, 55237) 1:5000 with blocking buffer and add 50 ul to each well, incubate 1 h at room temperature.
6. Substrate: Wash the plate 6 times, and add 50 ul/well of TMB substrate solution (BD Bioscience, 555214) incubate the plate for 5 to 10 min at room temperature in the dark. Add 25 ul/well of 1M $H_2SO_4$ to stop the reaction. Measure OD within 10 min at 450 nM.

Interpretation of Results: As described in Example 2.

Example 6

Specificity of the iC3b Assay

The specificity of the assay for iC3b described in Example 5 was tested using mock samples containing purified complement components either individually or in mixtures. C3 and C3b were the C3 products found to possess the highest degree of crosstalk with iC3b.

Figure 5:
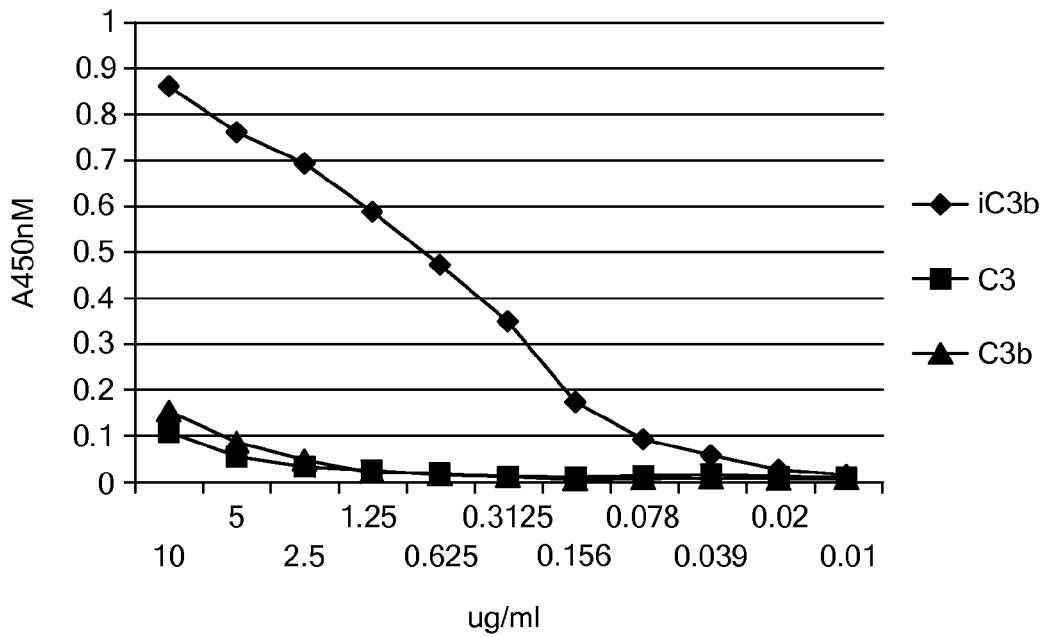
FIG. 5 shows a set of graphs demonstrating specificity of the iC3b assay. Equal amounts of human purified complement proteins C3, C3b and iC3b were used in the assay. The starting concentration of each component is 10 µg/ml in the leftmost well. Each sample was then diluted twofold per well across the plate.

To demonstrate the specificity of the assay, in one set of experiments equal amounts of human purified complement proteins C3, C3b and iC3b were loaded into the left most well of each row of a 96-well plate. The starting concentration of each component was 10 μg/ml in the leftmost well. The diluent was blocking buffer. Twofold dilutions of each sample were then made moving rightward across the plate. The concentration of iC3b in each sample was measured using the assay described in Example 5. Results of a representative assay are shown in FIG. 5 and demonstrate that there is no significant crosstalk with either C3 or C3b when purified components are assayed.

Figure 6:
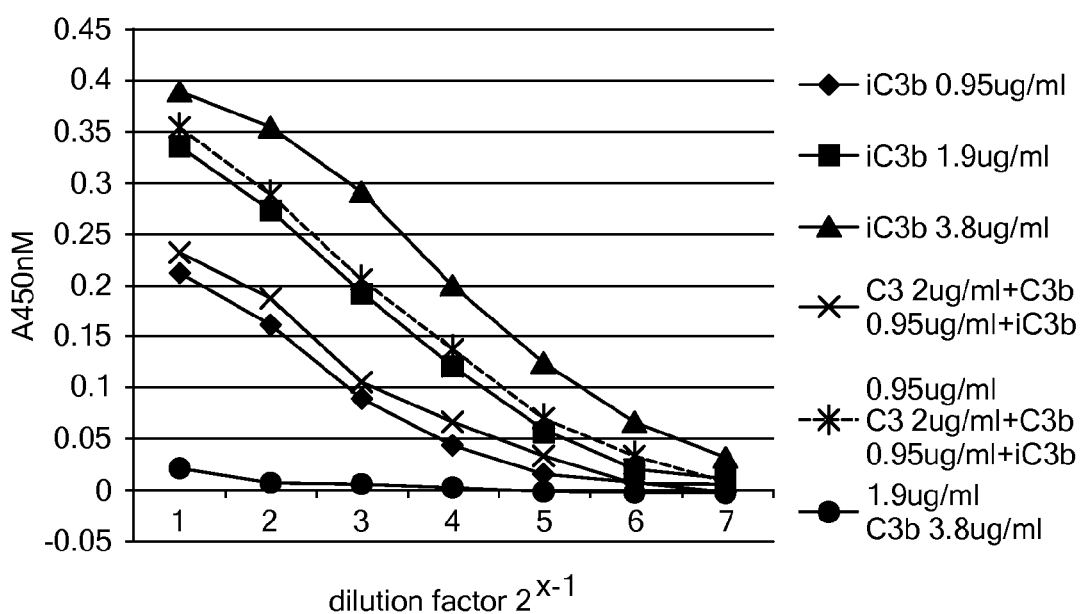
FIG. 6 shows results of the iC3b assay using mixed C3, C3b and iC3b protein. Each sample was diluted twofold per well across the plate.

In another set of experiments, iC3b was assayed in samples that contained various mixtures of C3, C3b and iC3b protein. Results of a representative assay are shown in FIG. 6 and demonstrate that there is no significant crosstalk with either C3 or C3b when mixtures of purified components are assayed. For example, the sample containing 0.95 iC3b (blue diamonds) gave virtually the same readout as the sample containing 0.95 μg/ml iC3b+0.95 μg/ml C3+2 μg/ml C3 (purple x).

Figure 7:
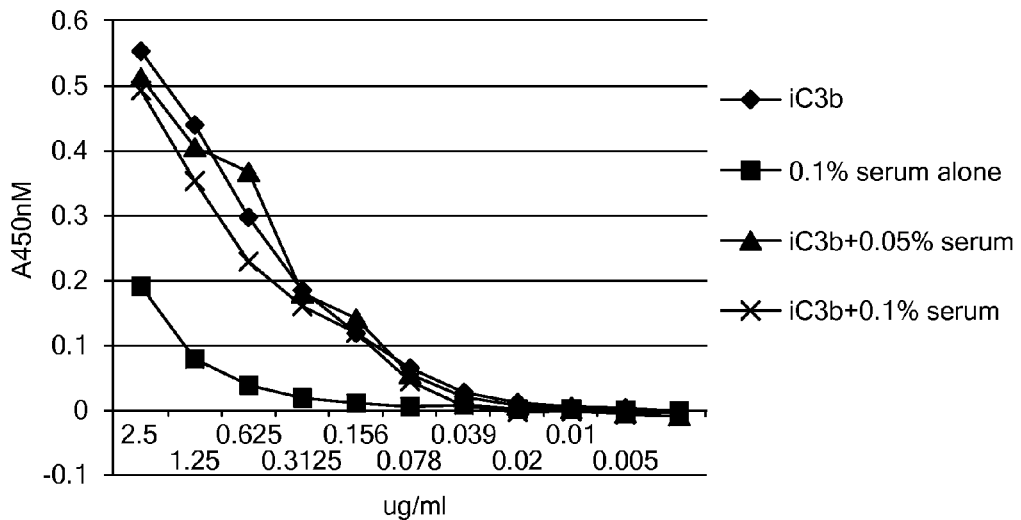
FIG. 7 shows a comparison of iC3b standard curves in blocking buffer. The concentration of iC3b was 2.5 µg/ml in the leftmost wells of the plate except for the 0.1% serum condition.

In other experiments, the assay was performed on samples that contained iC3b and varying concentrations of serum. FIG. 7 shows a comparison of iC3b standard curves in blocking buffer to which serum has been added. The concentration of iC3b was 2.5 μg/ml in the leftmost wells of the plate (except for the 0.1% serum condition). The data demonstrate that iC3b can be accurately measured in samples that contain serum.

Example 7

Measuring iC3b in Human Vitreous

Figure 8A:
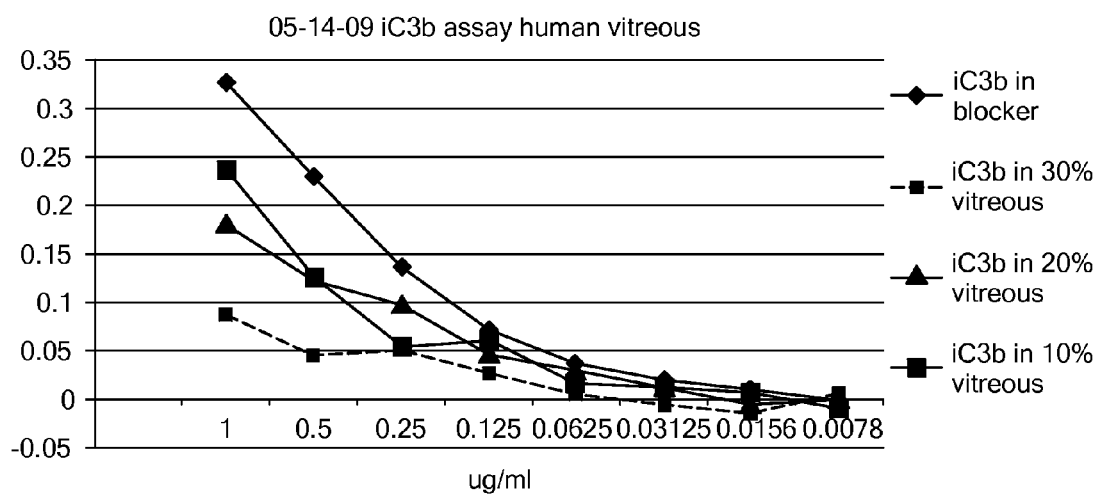
FIG. 8a shows detection of iC3b in human vitreous samples to which iC3b was added.

The assay for iC3b described in Example 5 was used to measure iC3b in samples containing normal human vitreous to which iC3b had been added. The vitreous was diluted to 10%, 20%, or 30% using blocking buffer. Results are shown in FIG. 8a. The raw and processed data are shown in Tables 6 and 7, respectively (FIG. 8b). Please note that the data in Tables 6 and 7 is oriented differently to that in Tables 2-5. Each set of 2 rows in Table 6 corresponds to duplicate samples. iC3b concentration decreases moving from left to right in columns 1-9. Columns 10-12 represent wells containing matrix only, as indicated. Values in Table 7 are obtained by averaging the corresponding duplicates in Table 6 and subtracting the relevant background value for matrix. For example, the value 0.049 in the row labeled 'iC3b in 20% vitreous' and column labeled '0.0125' iC3b concentration in Table 7 is obtained by averaging 0.361 and 0.384 from column 5, rows E and F of Table 6, and subtracting 0.328 (the 'matrix only' value for 20% vitreous in Table 6).

Example 8

Assay for Determining Concentration of Total C3

This example describes a method of determining the concentration of total C3 in human plasma or serum samples.
Definitions/Abbreviations
    PBS Phosphate Buffered Saline
    TMB Tetramethylbenzidine
Materials and Instruments
    Immulon 1B flat bottom Medium Binding 96-well plates (Thermo Electron Corporation, Cat #3355)
    2. Anti-human C3 HRP-conjugated polyclonal antibody (Cappel 55237)
    3. Murine anti-human C3d monoclonal antibody (Quidel, Cat#A207)
    4. Goat anti-mouse IgG HRP antibody (Jackson Immuno Labs, Cat #115-035-003)
    5. Blocking buffer: Starting block (PBS) Blocking Buffer (Thermo Electron Corporation, Cat#37538)
    6. TMB Substrate Reagent Set (BD Bioscience, Cat#555214)
    7. 1×PBS
    8. Wash buffer: 1×PBS with 0.05% Tween-20
    9. 1M $H_2SO_4$
    10. Plate reader capable of measuring absorbance at 450 nm
Procedure:
    Assay Preparation (for one 96-Well Plate)
    Capture Antibody: Dilute murine anti-human C3d antibody in 5 mL PBS for a final solution concentration of 2 ug/ml.
    Gently mix antibody by pipetting
    Coat an Immulon medium binding plate with 50 μl/well capture antibody in columns 1-12 and in duplicate (2) rows for each sample to be tested.
    Seal the plate and incubate overnight at 4° C. or at room temperature for 1 hour.

Shake and tap the plate to remove the coating antibody.
Block the plate with 200 μl per well of blocking buffer for 1 hour at room temperature.
Shake off the blocking buffer and wash the plate by filling with at least 300 μl/well washing buffer and then decant. Wash it 6× manually or by automatic plate washer.
Assay Procedure
Dilute human C3 protein in blocking buffer with a 5 μg/mL final concentration for the working dilution.
Dilute human serum or plasma in blocking buffer in a 1:250 dilution for the working dilution.
Add 200 μl of working sample or standard into the first well (column 1) of each row. From well 2 to 12, add 100 μl of blocking buffer. Serially dilute the samples by removing 100 ul of each standard or sample from column 1 of each row and adding it to the next well (column 2). Mix by pipetting 10 times. Continue this procedure for each subsequent well, stopping with column 11. Column 12 should remain as the blank, containing only blocking buffer. Cover the plate with plate sealer and incubate for 1 hour at room temperature.
Shake off samples and wash 6× as described above
Antibody Detection solution: Dilute 1 μl Anti-human C3 HRP-conjugated polyclonal antibody in 5 mL blocking buffer for a 1:5000 final concentration.
Add 50 μl/well of anti-C3 antibody detection solution, and incubate for 1 hour at room temperature.
Shake off antibody and wash 6× as described above.
Detection of reaction using TMB substrate—mix 5 mL of reagent A with 5 mL reagent B per test plate, no more than 10 minutes prior to use. Avoid exposure to light.
Add 100 μl/well of TMB substrate. Incubate for 2-5 minutes or until darkest color is approximately 1.2 OD.
Stop the reaction by adding 50 μl/well of 1M $H_2SO_4$
Read absorbance on plate reader at 450 nm wavelength.

Example 9

Assessing Intact C3 Levels in Individuals with AMD versus Controls

Protocol
Definitions/Abbreviations/Chemicals
PBS: Phosphate buffered saline without Ca++ and Mg++
EDTA: Ethylenediaminetetraacetic acid
TMB: Tetramethylenbenzidine substrate solution
H2SO4: Sulfuric Acid
Materials and Instruments
10×PBS: 10× Phosphate buffered saline without Ca++ and Mg++. (Cellgro, Mediatech Inc, Cat #: 46-013-CM).
Plate sealer: Denville Scientific, Inc, #B1212-45
EDTA: Gibco Invitrogen Corporation #15575-038
Tween 20: Molecular Biology Grade, (Promega Corporation Cat #H5151).
Blocking Buffer Thermo Scientific #37538
ELISA plate: Thermo Electron Corporation #3855
Mouse anti-human C3a/C3 Cell Sciences, #HM2075
Human C3: Complement Technologies, Inc #A113
Goat anti human C3-HRP: MP Biomedicals #55237
TMB: BD OptEIA, BD Biosciences Cat#555214)
H2SO4: 1M Sulfuric Acid
BIO-TEK ELX-405 ELISA microplate washer
BMG microplate reader
Procedure
0. General
0.1 Complement protein, serum samples and antibodies are kept on ice.
0.2 Avoid vortexing the samples during dilution, instead mix by slowly pipetting up and down or inverting the tubes a few times.
0.3 Thaw serum quickly in 37° C. water bath, and immediately transfer it to ice.
0.4 Do not let the wells dry out during the procedure.
0.5 Change pipetter tips during each serial dilution.
1.1 Prepare the Reagents and Cocktails as Detailed Below (for One Elisa Plate):
1.1.1 Preparation of stock 1×PBS
Dilute 100 ml 10×PBS stock in 900 ml distilled water
1.1.2 Preparation of stock Wash Buffer
Add 100 mL of 10×PBS and 0.5 mL Tween-20 to each 900 mL distilled water
1.1.3 Preparation of stock PBS-Tw-EDTA
Add 0.5 ml of Tween-20 and 20 mL of 500 mM EDTA stock to each 980 mL 1×PBS.
1.1.4 Preparation of coating antibody solution
Dilute 6 μL of mouse anti-human C3a/C3 (stock .1 mg/mL) into 6 mL of 1×PBS.
1.1.5 Preparation of C3 Standard (4 ug/mL)
Dilute 4 μl of human C3 (stock 1.0 mg/mL) into 1 mL of PBS-Tw-EDTA.
1.1.6 Preparation of detection antibody solution
Dilute 3 μl of goat anti C3-HRP into 6 mL of blocking buffer.
1.1.7 Preparation of TMB substrate
Prepare immediately before use, mix 3 mL of Reagent A with 3 mL of Reagent B.
1.2 Plate Coating:
1.2.1 Add 60 μL of the coating antibody solution to all wells, cover and incubate at 4° C. overnight or room temperature for 2 hours.
1.2.2 Throw out coating and tap on paper towels to dry.
1.3 Blocking
1.3.1 Add 200 μL of blocking buffer per well
1.3.2 Cover and incubate for 1-2 hours at room temperature
1.3.3 Wash plate 3 times with wash buffer
1.4 Preparing for Calibration Curve
1.4.1 C3 standard curve will be generated in triplicate or quadruplicate. All samples and standards will be diluted in PBS-Tw-EDTA. All serial dilutions will be done in tubes and then transferred to the plate. In seven empty 1.7 mL tubes add 300 ul of PBS-Tw-EDTA to each. Then add 300 ul of the standard stock solution to the first tube and mix five times. Change tips and take 300 ul from the first tube and add it to the second tube, mix five times and change tips. Continue until serial dilutions are complete. Add 50 ul of the dilutions to the wells as described in the template below:

|   | 1 | 2 | 3 | 4 | 5 | 6 | 7 | 8 | 9 | 10 | 11 | 12 |
|---|---|---|---|---|---|---|---|---|---|----|----|----|
| A | SD1 | SD1 | SD1 | | | | | | | | | |
| B | SD2 | SD2 | SD2 | | | | | | | | | |
| C | SD3 | SD3 | SD3 | | | | | | | | | |
| D | SD4 | SD4 | SD4 | | | | | | | | | |
| E | SD5 | SD5 | SD5 | | | | | | | | | |
| F | SD6 | SD6 | SD6 | | | | | | | | | |
| G | SD7 | SD7 | SD7 | | | | | | | | | |
| H | BC | BC | BC | | | | | | | | | |

SD: Standard Dilution
BC: Blank Control 1.4.2 Cover and incubate at room temperature for 1 hour.
1.4.3 Wash plate 6 times with wash buffer
1.5 Add HRP Conjugated Detection Antibody
1.5.1 Add 50 μL per well of the detection antibody solution and incubate plate at room temperature for 1 hour.

1.5.2 Wash plate 6 times with wash buffer.

1.6 Add Substrate

Add 50 μl of TMB substrate to each well and incubate for colorimetric reaction (5 to 15 minutes depending on sample concentration) Add 25 μl of 1M $H_2SO_4$ to each well to stop the reaction, and measure the absorbance at 450 nm;

1.7 Data Analysis 1.7.1 Absorbance versus concentration for the standard curve will be fitted to a four-parameter logistic regression (omit the first dilution of 2 μg/mL). Use the equation to back fit results to find the concentration of C3 in samples.

Results

Figure 9:
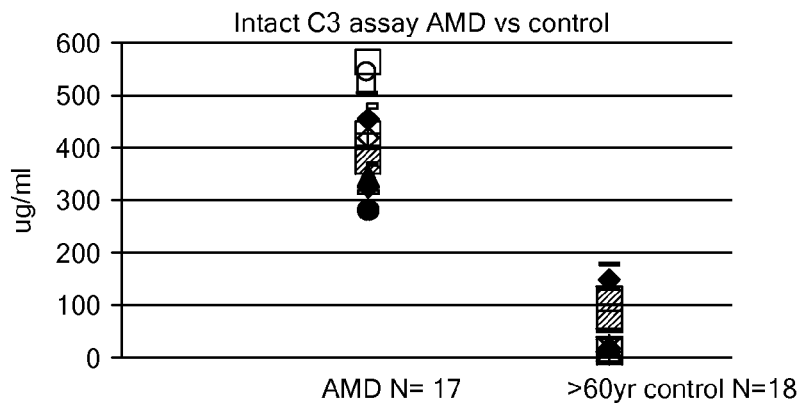
FIG. 9 is a graph showing levels of intact C3 in serum samples from subjects with AMD and in serum samples from control subjects more than 60 years of age.

The protocol set forth immediately above was used to assess intact C3 levels in serum samples obtained from individuals who had been diagnosed AMD (and in some cases their medications included Lucentis and/or anti-AMD vitamin preparations) and in control serum samples obtained from individuals more than 60 years of age who had not been diagnosed with AMD (but in at least some cases suffered from one or more other diseases). The samples were purchased from Bioreclamation, Inc. (Liverpool, N.Y.). The two sets of measurements were compared. FIG. 9 shows results of the assay. The values for thrree AMD and two non-AMD samples were out of range and were not included in the analysis.

It was found that levels of intact C3 were significantly higher in samples from individuals with AMD than in control samples. Levels of intact C3 in samples from individuals with AMD ranged between 314.4 μg/ml and 570.1 pg/m, while levels of intact C3 in samples from control individuals ranged between 10.18 μg/ml and 173.9 μg/ml. The intact C3 concentrations for the individual samples in μg/ml are shown below. The data represent the average of several replicates. Average values and standard deviations are readily calculated.

TABLE

| AMD Samples | Control Samples | AMD Samples | Control Samples |
|---|---|---|---|
| 457.1 | 146.5 | 540.9 | 14.81 |
| n/a | n/a | n/a | 18.95 |
| 348.2 | 5.734 | n/a | 14.79 |
| 417 | 108.6 | 570.2 | 6.116 |
| 383.5 | 72.16 | 545.6 | 10.18 |
| 282.8 | 13.83 | 430.1 | 7.504 |
| 374.6 | 74.15 | 479.5 | 9.834 |
| 369.4 | 13.27 | 506.2 | 125.2 |
| 314.3 | 173.9 | 420.2 | 10.9 |
| 325.9 | 20.39 | | |

Figure 10A:
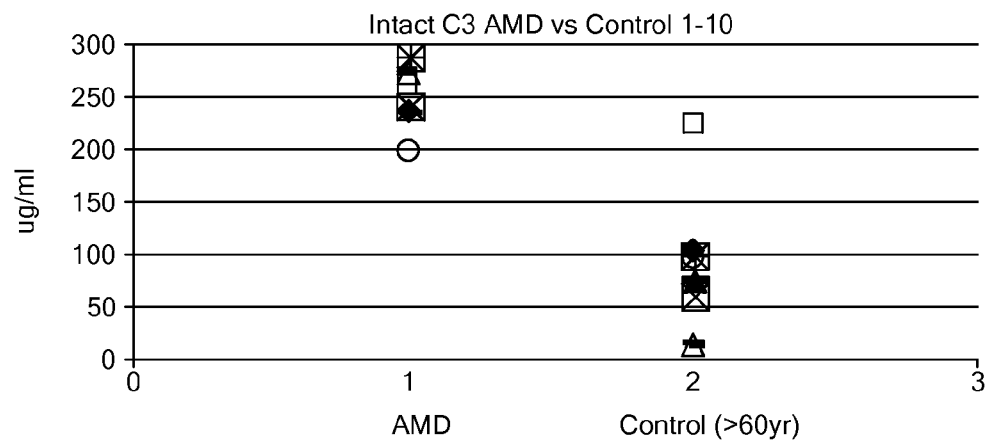
FIGS. 10a and 10b are graphs showing levels of intact C3 in serum samples from subjects with AMD and in serum samples from control subjects more than 60 years of age. The samples included the same samples used to generate the data shown in FIG. 9 and several additional samples.
Figure 10B:
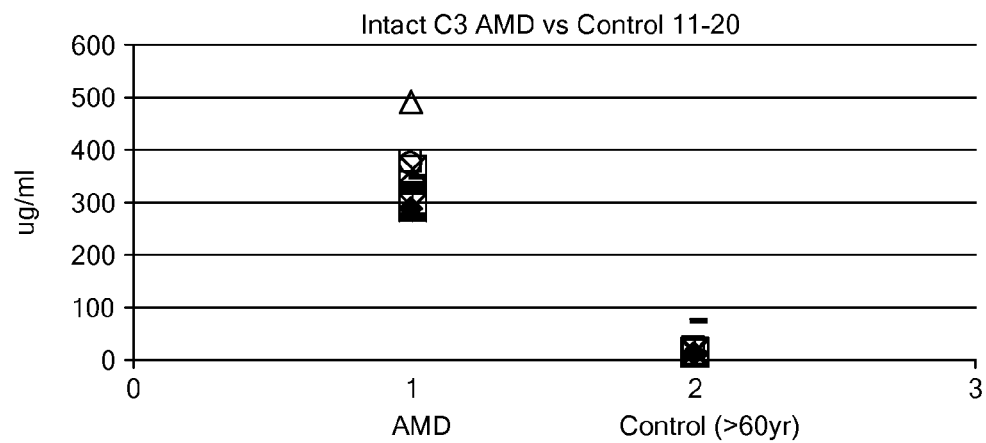

The assay was repeated using the same set of samples about 2 months later. The samples were divided into two sets of 10 AMD samples and two sets of 10 control samples. As shown in FIGS. 10a and 10b, similar results were obtained except that for one control sample, the intact C3 concentration was within the range measured for AMD samples. The intact C3 concentrations for the individual samples in mg/ml are shown below. The data represent the average of several replicates. Average values and standard deviations are readily calculated.

| 1 through 10 | | 11 through 20 | |
|---|---|---|---|
| AMD Samples 1 | Control Samples 2 | AMD 1 | Control 2 |
| 239.356 | 72.002 | 323.715 | 12.888 |
| 255.739 | 214.855 | 374.919 | 21.316 |
| 269.789 | 14.89 | 488.163 | 18.443 |
| 233.476 | 65.376 | 311.757 | 10.245 |
| 284.729 | 102.903 | 290.958 | 19.119 |
| 196.58 | 100.267 | 372.779 | 8.7786 |
| 234.449 | 59.131 | 365.226 | 17.354 |
| 224.373 | 14.2 | 343.141 | 73.758 |
| 268.204 | 16.151 | 271.581 | 12.94 |
| 225.902 | 104.644 | 287.322 | 11.764 |

The above results show that individuals with AMD can be distinguished from those not having AMD based on serum concentrations measured using the assay.

Example 10

Assay for Complement Activation in Individuals with Early AMD

Serum samples are obtained from a group of subjects with early AMD. The methods described in Examples 2 and 4 are used to measure intact C3 and iC3b in each of the samples. For each sample, the ratio of iC3b to intact C3 is obtained to assess the extent of complement activation. The subjects are monitored over the subsequent 3 years for progression, e.g., to advanced AMD (geographic atrophy and/or exudative AMD). During this time period, serum samples are obtained at intervals and complement activation is assessed by determining the ratio of iC3b to intact C3. Correlations are made between the extent of complement activation and the rapidity and/or likelihood of progression to advanced AMD. The information is used to develop a test to determine the likelihood of progression from early to advanced AMD.

Example 11

Assay for Intact C3 Levels in Individuals with AMD

Serum samples are obtained from between 50 and 5000 subjects exhibiting various stages of AMD (AREDS 2-4) and from between 50 and 5000 subjects at least 55 years of age who do not have AMD (AREDS 1). The subjects may be screened, and those will illnesses or other conditions that may acutely affect the level of intact C3 or the accuracy of the assay may be excluded. The method described in Example 10 is used to measure the level of intact C3 in the samples. Correlations between the level of intact C3 and AMD stage are determined Standard statistical methods may be used. The subjects without AMD are monitored over the subsequent 3 years for development of clinically evident AMD. The subjects with AMD are monitored over the subsequent 3 years for progression, e.g., from AREDS 2 stage to advanced AMD (with geographic atrophy and/or exudative AMD). During this time period, serum samples are obtained at intervals (e.g., every 1-3 months) and the level of intact C3 is assessed. Correlations between the level of intact C3 and the rapidity and/or likelihood of progression to advanced AMD are determined Standard statistical methods may be used. Analyses are performed on the entire subject groups and on subsets composed of subjects with particular risk factors such as smoking or genetic background or in different age brackets. For example, analyses are performed on subjects with genotypes associated with AMD risk (e.g., having various CFH polymorphisms). The information is used to further refine the methods of using the level of intact C3 to provide improved prognostic, diagnostic, and/or therapeutic information relating to AMD development or progression.

\* \* \*

Those skilled in the art will recognize, or be able to ascertain using no more than routine experimentation, many equivalents to the specific embodiments of the invention described herein. The scope of the present invention is not intended to be limited to the embodiments described above, but rather is as set forth in the claims. In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention provides embodiments in which exactly one member of the group is present in, employed in, or otherwise relevant to a given product or process. The invention also provides embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more elements or limitations found in any other claim that is dependent on the same base claim. Furthermore, where the claims recite a composition, it is to be understood that methods of administering the composition according to any of the methods disclosed herein, and methods of using the composition for any of the purposes disclosed herein are provided, and methods of making the composition according to any of the methods of making disclosed herein are provided, unless otherwise indicated or unless it would be evident to one of ordinary skill in the art that a contradiction or inconsistency would arise. It should also be understood that references herein to "the invention" or to materials of use in the invention or to applications or uses of the invention can refer to one embodiment or aspect of the invention, or to more than one embodiment or aspect of the invention, and should not be interpreted as limiting.

Where elements are presented as lists or groups, it is to be understood that each subgroup of the elements is also disclosed, and any element(s) can be removed from the group. For purposes of conciseness only some of these embodiments have been specifically recited individually and specifically herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

In certain embodiments of any of the methods of the invention for assessing complement activation or proteolytic activity, the method further can comprise a step of providing a sample obtained from subject suffering from or at risk of a complement deficiency or a complement-mediated disorder or clinical condition. In certain embodiments of any of the methods of the invention for assessing complement activation or proteolytic activity, the method further can comprise diagnosing a subject as suffering from or at risk of a complement deficiency or a complement-mediated disorder or clinical condition. In certain embodiments of any of the methods of the invention for assessing complement activation or proteolytic activity, the method can further comprise administering a complement modulating agent to the subject.

Where ranges are given herein, the invention provides embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. A time period of 1 month is understood to mean 30 days. A time period of 1 year is understood to mean 365 days. For any embodiment of the invention in which a numerical value is prefaced by "about" or "approximately", the invention provides an embodiment in which the exact value is recited. For any embodiment of the invention in which a numerical value is not prefaced by "about" or "approximately", the invention provides an embodiment in which the value is prefaced by "about" or "approximately".

Any particular embodiment, feature, or aspect of the present invention may be explicitly excluded from any one or more of the claims.

We claim:

1. A method of assessing complement activation in a sample, the method either comprising steps of:
   (a) capturing intact C3 present in the sample or in a sub-sample thereof using an antibody that specifically binds to at least one epitope that is present in intact C3;
   (b) quantifying intact C3 captured in step (a) using an antibody that specifically binds to at least one epitope of intact C3 and has a detectable label directly or indirectly linked thereto;
   (c) capturing iC3b present in the sample or in a sub-sample thereof using an antibody that specifically binds to a neoepitope of iC3b;
   (d) quantifying iC3b captured in step (c) using an antibody that specifically binds to at least one epitope of iC3b and has a detectable label directly or indirectly linked thereto; and
   (e) calculating the ratio of iC3b to intact C3 using the results of (b) and (d) or comprising steps of:
   (i) capturing intact C3 present in the sample or in a sub-sample thereof using an antibody that specifically binds to at least one epitope that is present in intact C3;
   (ii) quantifying intact C3 captured in step (i) using an antibody that specifically binds to at least one epitope of intact C3 and has a detectable label directly or indirectly linked thereto;
   (iii) capturing total C3 present in the sample or in a sub-sample thereof using an antibody that binds to total C3, wherein the antibody specifically binds to at least one epitope that is present in total C3;
   (iv) quantifying total C3 captured in step (iii) using an antibody that specifically binds to at least one epitope of C3c or C3d and has a detectable label directly or indirectly linked thereto; and
   (v) calculating the relative concentration of intact C3 and total C3 in the sample using the results of (ii) and (iv).

2. The method of claim 1, wherein the antibody of step (a) or step (i) is a monoclonal antibody that specifically binds to an epitope present in C3a/C3.

3. The method of claim 1, wherein the sample comprises whole blood, plasma, or serum.

4. The method of claim 1, wherein the sample comprises an agent being assessed for its ability to modulate complement activation.

5. The method of claim 1, wherein the method comprises performing steps (a)-(e).

6. The method of claim 5, wherein step (a) comprises capturing intact C3 using a monoclonal antibody that specifically binds to an epitope present in C3a/C3, and step (b) comprises detecting intact C3 using a polyclonal antibody that specifically binds to at least one epitope present in C3 and has a detectable label directly or indirectly linked thereto.

7. The method of claim 5, wherein step (c) comprises capturing iC3b using a monoclonal antibody that specifically binds to a neoepitope of iC3b, and step (d) comprises detecting iC3b using a polyclonal antibody that specifically binds to at least one epitope present in iC3b, and has a detectable label directly or indirectly linked thereto.

8. The method of claim 1, wherein the method comprises performing steps (i)-(v).

9. The method of claim 8, wherein the capture antibody of step (i) comprises an antibody that specifically binds to at least one epitope present in C3d.

10. The method of claim 8, wherein the capture antibody that binds to total C3 is a polyclonal antibody that specifically binds to at least one epitope present in C3d and intact C3 is detected using a monoclonal antibody that specifically binds to an epitope present in C3a and has a detectable label directly or indirectly linked thereto.

11. The method of claim 1, wherein the method comprises determining the ratio of iC3b to intact C3, further comprising determining the concentration of total C3 in the sample.

12. The method of claim 1, wherein the antibody used to capture intact C3 is a monoclonal antibody that binds to intact C3 and is specific for C3 as compared with iC3b or C3b.

13. The method of claim 12, wherein the monoclonal antibody is anti-human C3a/C3 antibody HM2075 or an antibody that is at least as specific for intact C3 as compared with C3b, iC3b, C3c, and C3d as antibody clone 2898 (Hycult Biotechnology catalog number HM2075).

14. The method of claim 1, wherein iC3b is captured or quantified using a monoclonal antibody that binds to a neoepitope of iC3b and is specific for iC3b as compared with C3b or C3.

15. The method of claim 14, wherein the monoclonal antibody is A209 or an antibody that is at least as specific for iC3b as compared with C3b or C3 as monoclonal antibody A209 Quidel catalog number A209).

16. The method of claim 1, wherein the antibody that captures intact C3 is immobilized on a support comprising a microwell plate or a plurality of particles.

17. The method of claim 1, wherein the antibody that captures total C3 is immobilized on a support comprising a microwell plate or a plurality of particles.

18. A method of assessing complement activation in a sample, the method comprising steps of:
   (a) capturing and detecting intact C3, wherein intact C3 is captured using an antibody that specifically binds to at least one epitope present in C3a/C3 but does not bind to C3 fragments other than C3a; and
   (b) capturing and detecting iC3b, wherein iC3b is captured using an antibody that specifically binds to a neoepitope of iC3b, and
   (c) calculating the ratio of iC3b to intact C3 using the results of (a) and (b), wherein the ratio of iC3b to intact C3 serves as an indicator of the extent of complement activation.

19. The method of claim 18, wherein intact C3 is captured using a monoclonal antibody that specifically binds to an epitope present in C3a/C3 and is detected using a polyclonal antibody that specifically binds to at least one epitope present in C3 and has a detectable label directly or indirectly linked thereto.

20. The method of claim 18, wherein iC3b is captured using a monoclonal antibody that specifically binds to a neoepitope of iC3b and is detected using a polyclonal antibody that specifically binds to at least one epitope of iC3b and has a detectable label directly or indirectly linked thereto.

* * * * *

UNITED STATES PATENT AND TRADEMARK OFFICE
CERTIFICATE OF CORRECTION

| | |
|---|---|
| PATENT NO. | : 9,291,622 B2 |
| APPLICATION NO. | : 13/321522 |
| DATED | : March 22, 2016 |
| INVENTOR(S) | : Zhang et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 659 days.

Signed and Sealed this
Twelfth Day of July, 2016

Michelle K. Lee
*Director of the United States Patent and Trademark Office*

SEQUENCE LISTING

```
<160> NUMBER OF SEQ ID NOS: 36

<210> SEQ ID NO 1

<400> SEQUENCE: 1

000

<210> SEQ ID NO 2

<400> SEQUENCE: 2

000
```

```
<210> SEQ ID NO 3
<400> SEQUENCE: 3

000

<210> SEQ ID NO 4
<400> SEQUENCE: 4

000

<210> SEQ ID NO 5
<400> SEQUENCE: 5

000

<210> SEQ ID NO 6
<400> SEQUENCE: 6

000

<210> SEQ ID NO 7
<400> SEQUENCE: 7

000

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal H
<220> FEATURE:
<221> NAME/KEY: MOD_RES
<222> LOCATION: (13)..(13)
<223> OTHER INFORMATION: C-terminal CONH2

<400> SEQUENCE: 8

Ile Cys Val Val Gln Asp Trp Gly His His Arg Cys Thr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (13)..(13)
<223> OTHER INFORMATION: C-terminal CONH2

<400> SEQUENCE: 9

Ile Cys Val Val Gln Asp Trp Gly His His Arg Cys Thr
1               5                   10
```

```
<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (13)..(13)
<223> OTHER INFORMATION: C-terminal CONH2

<400> SEQUENCE: 10

Ile Cys Val Tyr Gln Asp Trp Gly Ala His Arg Cys Thr
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (13)..(13)
<223> OTHER INFORMATION: C-terminal COOH

<400> SEQUENCE: 11

Ile Cys Val Trp Gln Asp Trp Gly Ala His Arg Cys Thr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (13)..(13)
<223> OTHER INFORMATION: C-terminal CONH2

<400> SEQUENCE: 12

Ile Cys Val Trp Gln Asp Trp Gly Ala His Arg Cys Thr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
```

```
<222> LOCATION: (13)..(13)
<223> OTHER INFORMATION: d-Thr
<220> FEATURE:
<221> NAME/KEY: MOD_RES
<222> LOCATION: (13)..(13)
<223> OTHER INFORMATION: C-terminal COOH

<400> SEQUENCE: 13

Ile Cys Val Trp Gln Asp Trp Gly Ala His Arg Cys Thr
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 2-napthylalanine
<220> FEATURE:
<221> NAME/KEY: MOD_RES
<222> LOCATION: (13)..(13)
<223> OTHER INFORMATION: C-terminal CONH2

<400> SEQUENCE: 14

Ile Cys Val Ala Gln Asp Trp Gly Ala His Arg Cys Thr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 2-naphthylalanine
<220> FEATURE:
<221> NAME/KEY: MOD_RES
<222> LOCATION: (13)..(13)
<223> OTHER INFORMATION: C-terminal COOH

<400> SEQUENCE: 15

Ile Cys Val Ala Gln Asp Trp Gly Ala His Arg Cys Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
```

-continued

```
<223> OTHER INFORMATION: 1-naphthylalanine
<220> FEATURE:
<221> NAME/KEY: MOD_RES
<222> LOCATION: (13)..(13)
<223> OTHER INFORMATION: C-terminal COOH

<400> SEQUENCE: 16

Ile Cys Val Ala Gln Asp Trp Gly Ala His Arg Cys Thr
 1               5                  10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 2-indanylglycine carboxylic acid
<220> FEATURE:
<221> NAME/KEY: MOD_RES
<222> LOCATION: (13)..(13)
<223> OTHER INFORMATION: C-terminal CONH2

<400> SEQUENCE: 17

Ile Cys Val Gly Gln Asp Trp Gly Ala His Arg Cys Thr
 1               5                  10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 2-indanylglycine carboxylic acid
<220> FEATURE:
<221> NAME/KEY: MOD_RES
<222> LOCATION: (13)..(13)
<223> OTHER INFORMATION: C-terminal COOH

<400> SEQUENCE: 18

Ile Cys Val Gly Gln Asp Trp Gly Ala His Arg Cys Thr
 1               5                  10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATOIN
<220> FEATURE:
<221> NAME/KEY: MOD_RES
<222> LOCATION: (4)..(4)
<223> OTHER INFORMATION: dihydrotrpytophan
```

```
<220> FEATURE:
<221> NAME/KEY: MISC_FEATURE
<222> LOCATION: (13)..(13)
<223> OTHER INFORMATION: C-terminal COOH

<400> SEQUENCE: 19

Ile Cys Val Trp Gln Asp Trp Gly Ala His Arg Cys Thr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 4-benzoyl-L-phenylalanine
<220> FEATURE:
<221> NAME/KEY: MOD_RES
<222> LOCATION: (13)..(13)
<223> OTHER INFORMATION: C-terminal COOH

<400> SEQUENCE: 20

Ile Cys Val Phe Gln Asp Trp Gly Ala His Arg Cys Thr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: p-benzoyl-L-phenylalanine
<220> FEATURE:
<221> NAME/KEY: MOD_RES
<222> LOCATION: (13)..(13)
<223> OTHER INFORMATION: C-terminal CONH2

<400> SEQUENCE: 21

Ile Cys Val Phe Gln Asp Trp Gly Ala His Arg Cys Thr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: Bta
<220> FEATURE:
```

```
<221> NAME/KEY: MOD_RES
<222> LOCATION: (13)..(13)
<223> OTHER INFORMATION: C-terminal COOH

<400> SEQUENCE: 22

Ile Cys Val Xaa Gln Asp Trp Gly Ala His Arg Cys Thr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: Bta
<220> FEATURE:
<221> NAME/KEY: MOD_RES
<222> LOCATION: (13)..(13)
<223> OTHER INFORMATION: C-terminal CONH2

<400> SEQUENCE: 23

Ile Cys Val Xaa Gln Asp Trp Gly Ala His Arg Cys Thr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (9)..(9)
<223> OTHER INFORMATION: 2-alpha-aminobutyric acid
<220> FEATURE:
<221> NAME/KEY: MOD_RES
<222> LOCATION: (13)..(13)
<223> OTHER INFORMATION: C-terminal CONH2

<400> SEQUENCE: 24

Ile Cys Val Trp Gln Asp Trp Gly Xaa His Arg Cys Thr
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal H
<220> FEATURE:
<221> NAME/KEY: MOD_RES
<222> LOCATION: (16)..(16)
<223> OTHER INFORMATION: C-terminal COOH

<400> SEQUENCE: 25
```

Gly Ile Cys Val Trp Gln Asp Trp Gly Ala His Arg Cys Thr Ala Asn
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 5-fluoro-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 26

Ile Cys Val Trp Gln Asp Trp Gly Ala His Arg Cys Thr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 5-methyl-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 27

Ile Cys Val Trp Gln Asp Trp Gly Ala His Arg Cys Thr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal Ac
<220> FEATURE:
<221> NAME/KEY: MOD_RES
<222> LOCATION: (4)..(4)
<223> OTHER INFORMATION: 1-methyl-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 28

Ile Cys Val Trp Gln Asp Trp Gly Ala His Arg Cys Thr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (7)..(7)
<223> OTHER INFORMATION: 5-fluoro-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 29

Ile Cys Val Trp Gln Asp Trp Gly Ala His Arg Cys Thr
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 5-fluoro-L-tryptophan
<220> FEATURE:
<221> NAME/KEY: MOD_RES
<222> LOCATION: (7)..(7)
<223> OTHER INFORMATION: 5-fluoro-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 30

Ile Cys Val Trp Gln Asp Trp Gly Ala His Arg Cys Thr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 5-methyl-L-tryptophan
<220> FEATURE:
<221> NAME/KEY: MOD_RES
<222> LOCATION: (7)..(7)
<223> OTHER INFORMATION: 5-fluoro-L-tryptophan

```
<220> FEATURE:
<221> NAME/KEY: MOD_RES
<222> LOCATION: (13)..(13)
<223> OTHER INFORMATION: C-terminal CONH2

<400> SEQUENCE: 31

Ile Cys Val Trp Gln Asp Trp Gly Ala His Arg Cys Thr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 1-methyl-L-tryptophan
<220> FEATURE:
<221> NAME/KEY: MOD_RES
<222> LOCATION: (7)..(7)
<223> OTHER INFORMATION: 5-fluoro-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 32

Ile Cys Val Trp Gln Asp Trp Gly Ala His Arg Cys Thr
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-term H
<220> FEATURE:
<221> NAME/KEY: MOD_RES
<222> LOCATION: (5)..(5)
<223> OTHER INFORMATION: 6-fluoro-L-tryptophan
<220> FEATURE:
<221> NAME/KEY: MOD_RES
<222> LOCATION: (8)..(8)
<223> OTHER INFORMATION: 6-fluoro-L-tryptophan
<220> FEATURE:
<221> NAME/KEY: MOD_RES
<222> LOCATION: (15)..(15)
<223> OTHER INFORMATION: C-terminal COOH

<400> SEQUENCE: 33

Gly Ile Cys Val Trp Gln Asp Trp Gly Ala His Arg Cys Thr Asn
1               5                   10                  15

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 1-formyl-Trp
<220> FEATURE:
<221> NAME/KEY: MOD_RES
<222> LOCATION: (13)..(13)
<223> OTHER INFORMATION: C-terminal CONH2

<400> SEQUENCE: 34

Ile Cys Val Trp Gln Asp Trp Gly Ala His Arg Cys Thr
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: MOD_RES
<222> LOCATION: (4)..(4)
<223> OTHER INFORMATION: 1-methoxy-tryptophan
<220> FEATURE:
<221> NAME/KEY: MISC_FEATURE
<222> LOCATION: (13)..(13)
<223> OTHER INFORMATION: C-terminal CONH2

<400> SEQUENCE: 35

Ile Cys Val Trp Gln Asp Trp Gly Ala His Arg Cys Thr
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-term H
<220> FEATURE:
<221> NAME/KEY: MOD_RES
<222> LOCATION: (5)..(5)
<223> OTHER INFORMATION: 5-fluoro-L-tryptophan
<220> FEATURE:
<221> NAME/KEY: MOD_RES
<222> LOCATION: (8)..(8)
<223> OTHER INFORMATION: 5-fluoro-L-tryptophan
<220> FEATURE:
<221> NAME/KEY: MOD_RES
<222> LOCATION: (15)..(15)
<223> OTHER INFORMATION: C-terminal COOH

<400> SEQUENCE: 36

Gly Ile Cys Val Trp Gln Asp Trp Gly Ala His Arg Cys Thr Asn
1               5                   10                  15
```